(12) United States Patent
Bowie et al.

(10) Patent No.: US 10,196,653 B2
(45) Date of Patent: Feb. 5, 2019

(54) SYNTHETIC BIOCHEMISTRY MOLECULAR PURGE VALVE MODULE THAT MAINTAIN CO-FACTOR BALANCE

(71) Applicant: The Regents of the University of California, Oakland, CA (US)

(72) Inventors: James U. Bowie, Culver City, CA (US); Paul H. Opgenorth, Los Angeles, CA (US); Tyler P. Korman, Sierra Madre, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/127,351

(22) PCT Filed: Apr. 2, 2015

(86) PCT No.: PCT/US2015/024181
§ 371 (c)(1),
(2) Date: Sep. 19, 2016

(87) PCT Pub. No.: WO2015/153929
PCT Pub. Date: Oct. 8, 2015

(65) Prior Publication Data
US 2017/0183688 A1   Jun. 29, 2017

Related U.S. Application Data

(60) Provisional application No. 61/974,311, filed on Apr. 2, 2014.

(51) Int. Cl.
*C12P 5/00* (2006.01)
*C12N 9/10* (2006.01)
*C12P 7/62* (2006.01)
*C12N 9/02* (2006.01)

(52) U.S. Cl.
CPC ............ *C12P 5/007* (2013.01); *C12N 9/0008* (2013.01); *C12N 9/1029* (2013.01); *C12P 7/625* (2013.01); *C12Y 102/01051* (2013.01); *C12Y 106/99001* (2013.01); *C12Y 108/01004* (2013.01); *C12Y 203/01012* (2013.01)

(58) Field of Classification Search
CPC .............................. C12P 5/007; C12N 9/0008
See application file for complete search history.

(56) References Cited

U.S. PATENT DOCUMENTS

2014/0058056 A1    2/2014  Burgard et al.

FOREIGN PATENT DOCUMENTS

WO    2010/051527 A2    5/2010

OTHER PUBLICATIONS

Bologna et al. 2007; *Escherichia coli* malic enzymes: Two isoforms with substantial differences in kinetic properties, metabolic regulation, and structure. J. Bacteriol. 189(16): 5937-5946.*
Nickitas-Etienne, International Preliminary Report on Patentability and Written Opinion, PCT/US2015/024181, The International Bureau of WIPO, dated Oct. 13, 2016.
Thomas, Shane, International Search Report and Written Opinion, PCT/US2015/024181, United States Patent and Trademark Office, dated Sep. 18, 2015.
Opgenorth et al., "A synthetic biochemistry molecular purge valve module that maintains redox balance," Nat. Commun., vol. 5, pp. 4113, Jun. 17, 2014.
Heux et al., "Cofactor engineering in *Saccharomyces cerevisiae*: Expression of H2O-forming NADH oxidase and impact on redox metabolism", Metabolic Engineering, 8:4, Jul. 1, 2006 (published online Feb. 10, 2006), pp. 303-314.
Korman et al., "A synthetic biochemistry system for the in vitro production of isoprene from glycolysis intermediates", Protein Science, 23:5, Mar. 12, 2014 (published online Feb. 6, 2014), pp. 576-585.
Niebuhr-Ebel, K., Extended European Search Report, Application No. 15774454.1, European Patent Office, dated Jul. 17, 2017.
Satoh et al., "Enzyme-catalyzed poly(3-hydroxybutyrate) synthesis from acetate with CoA recycling and NADPH regeneration in vitro", Journal of Bioscience of Bioengineering, 95:4, Jan. 1, 2003, pp. 335-341.

* cited by examiner

*Primary Examiner* — Karen Cochrane Carlson
(74) *Attorney, Agent, or Firm* — Gavrilovich, Dodd & Lindsey LLP

(57) ABSTRACT

The disclosure provides a metabolic pathway for producing a metabolite, the metabolic pathway having a co-factor purge valve system for recycling a cofactor used in the metabolic pathway.

18 Claims, 7 Drawing Sheets

Specification includes a Sequence Listing.

SYNTHETIC BIOCHEMISTRY MOLECULAR PURGE VALVE MODULE THAT MAINTAIN CO-FACTOR BALANCE

STATEMENT REGARDING FEDERALLY SPONSORED RESEARCH

This invention was made with Government support under Grant Number DE-FC02-02ER63421, awarded by the U.S. Department of Energy. The Government has certain rights in the invention.

CROSS REFERENCE TO RELATED APPLICATIONS

This application is a U.S. National Stage Application filed under 35 U.S.C. § 371 and claims priority to International Application No. PCT/US2015/024181, filed Apr. 2, 2015, which application claims priority to U.S. Provisional Application Ser. No. 61/974,311, filed Apr. 2, 2014, the disclosures of which are incorporated herein by reference.

TECHNICAL FIELD

The disclosure provides engineered pathways for chemical production using a cofactor balancing molecular purge system.

BACKGROUND

The greatest potential environmental benefit of metabolic engineering would be the production of low value/high volume commodity chemicals, such as biofuels. Yet the high yields required for the economic viability of low-value chemicals is particularly hard to achieve in microbes due to the myriad competing biochemical pathways needed for cell viability.

SUMMARY

The disclosure provides a recombinant, artificial or engineered metabolic pathway comprising a plurality of enzymatic steps that converts a substrate to a product, wherein the pathway includes an unbalanced production and utilization of a co-factor the pathway comprising a non-naturally occurring purge valve pathway that recycles the co-factor, wherein the purge valve pathway comprises an enzyme that uses the co-factor to convert a metabolite in one or more of the plurality of enzymatic steps. In one embodiment, the recombinant, artificial or engineered metabolic pathway comprises (a) a first enzymatic step that converts a first metabolite to a second metabolite using a first co-factor; (b) a second enzymatic step that converts the first metabolite to the second metabolite using a second co-factor; and (c) a third enzymatic step that converts the second or a third metabolite to an intermediate or the product using the second cofactor; wherein when the co-factor utilization become unbalanced between the first and second cofactor, the purge valve pathway purges the excess co-factor. In a further embodiment of either of the foregoing the co-factors are oxidizing/reducing co-factors. In a further embodiment, the oxidizing/reducing co-factors are $NAD^+/NADH$, $NADP^+/NADPH$ or $FAD^+/FADH$. In another embodiment of any of the foregoing the first cofactor comprises $NAD^+/NADH$ and the second cofactor comprises $NADP^+/NADPH$. In another embodiment of any of the foregoing the purge valve pathway comprises a NADH dehydrogenase, and NADPH dehydrogenase and an NADH oxidase. In a further embodiment, the NADH dehydrogenase is a NADH pyruvate dehydrogenase complex. In still a further embodiment, the NADH pyruvate dehydrogenase complex comprises a pyruvate dehydrogenase subunit a, a pyruvate dehydrogenase subunit b, a dihydrolipoamide acetyltransferase, and a dihydrolipoamide dehydrogenase. In yet a further embodiment, the pyruvate dehydrogenase subunit a comprises a sequence that is at least 90%, 91%, 92%, 93%, 94%, 95%, 96%, 97%, 98%, 99% or 100% identical to SEQ ID NO:1, wherein the pyruvate dehydrogenase subunit b comprises a sequence that is at least 90%, 91%, 92%, 93%, 94%, 95%, 96%, 97%, 98%, 99% or 100% identical to SEQ ID NO:2, wherein the dihydrolipoamide acetyltransferase is at least 90%, 91%, 92%, 93%, 94%, 95%, 96%, 97%, 98%, 99% or 100% identical so SEQ ID NO:3, and wherein the dihydrolipoamide dehydrogenase is at least 90%, 91%, 92%, 93%, 94%, 95%, 96%, 97%, 98%, 99% or 100% identical to SEQ ID NO:5, wherein the complex converts pyruvate to acetyl-CoA. In yet a further embodiment, the NADPH dehydrogenase is a NADPH pyruvate dehydrogenase complex. In a further embodiment, the NADPH pyruvate dehydrogenase complex comprises a pyruvate dehydrogenase subunit a, a pyruvate dehydrogenase subunit b, a dihydrolipoamide acetyltransferase, and a mutant dihydrolipoamide dehydrogenase the preferentially uses $NADP^+$. In another embodiment, the pyruvate dehydrogenase subunit a comprises a sequence that is at least 90%, 91%, 92%, 93%, 94%, 95%, 96%, 97%, 98%, 99% or 100% identical to SEQ ID NO:1, wherein the pyruvate dehydrogenase subunit b comprises a sequence that is at least 90%, 91%, 92%, 93%, 94%, 95%, 96%, 97%, 98%, 99% or 100% identical to SEQ ID NO:2, wherein the dihydrolipoamide acetyltransferase is at least 90%, 91%, 92%, 93%, 94%, 95%, 96%, 97%, 98%, 99% or 100% identical so SEQ ID NO:3, and wherein the dihydrolipoamide dehydrogenase is at least 90%, 91%, 92%, 93%, 94%, 95%, 96%, 97%, 98%, 99% or 100% identical to SEQ ID NO:7 and preferentially uses $NADP^+$, wherein the complex converts pyruvate to acetyl-CoA. In yet further embodiments, the NADH oxidase is a NoxE or homolog thereof. In a further embodiment, the NADH oxidase comprises a sequence that is at least 90%, 91%, 92%, 93%, 94%, 95%, 96%, 97%, 98%, 99% or 100% identical to SEQ ID NO:10. In another embodiment of any of the foregoing the pathway is a cell-free system. In still another embodiment, the recombinant, artificial or engineered pathway produces PHB. In yet another embodiment, the recombinant, artificial or engineered pathway produces isoprene.

The disclosure also provides an enzymatic system comprising a metabolic pathway including a plurality of enzymes for converting a substrate to a product, the metabolic pathway having an unbalanced utilization of reducing/oxidizing cofactors, wherein the enzymatic system comprises a metabolic purge valve comprising an NADH pyruvate dehydrogenase, and NADPH pyruvate dehydrogenase and a NADH/NADPH oxidase.

The disclosure also provides a recombinant microorganism comprising a heterologous NADH pyruvate dehydrogenase, a NADPH pyruvate dehydrogenase and a NADH and/or NADPH oxidase.

The disclosure also provides a recombinant polypeptide comprising a sequence that is at least 90%, 91%, 92%, 93%, 94%, 95%, 96%, 97%, 98%, 99% or 100% identical to SEQ ID NO:5 and comprising the mutations E206V, G207R, A208K, and S213R. In one embodiment, the polypeptide comprises the sequence of SEQ ID NO:7.

The disclosure also provides a polynucleotide encoding a polypeptide comprising a sequence that is at least 90%, 91%, 92%, 93%, 94%, 95%, 96%, 97%, 98%, 99% or 100% identical to SEQ ID NO:5 and comprising the mutations E206V, G207R, A208K, and S213R. In a further embodiment, the polynucleotide encodes a polypeptide of SEQ ID NO:7. In a further embodiment, the polynucleotide comprises a sequence that is 70-90%, 91%, 92%, 93%, 94%, 95%, 96%, 97%, 98%, 99% or 100% identical to SEQ ID NO:6 and encodes a polypeptide of SEQ ID NO:7.

The disclosure provides a recombinant, artificial or engineered pathway that converts a substrate to a desired product, wherein the pathway includes an unbalanced production and utilization of a cofactor the pathway comprising a first metabolic step that produces a first reduced cofactor and a second metabolic step that oxidizes the first reduced cofactor, wherein the pathway comprises a purge valve pathway that recycles a second reduced cofactor. In one embodiment, the first reduced cofactor comprises NADPH and the second reduced cofactor comprises NADH. In a further embodiment, the purge valve pathway comprises a NADH dehydrogenase and an NADH oxidase. In still a further embodiment, the NADH dehydrogenase is a NADH pyruvate dehydrogenase. In another embodiment, the first reduced cofactor comprises NADH and the second reduced cofactor comprises NADPH. In yet another embodiment, the purge valve pathway comprises a NADPH dehydrogenase and an NADPH oxidase. In a further embodiment, the NADPH dehydrogenase is a NADPH pyruvate dehydrogenase. In another embodiment of any of the foregoing claims the pathway produces isoprene from pyruvate. In yet another embodiment of any of the foregoing claims the pathway produces PHB.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1:
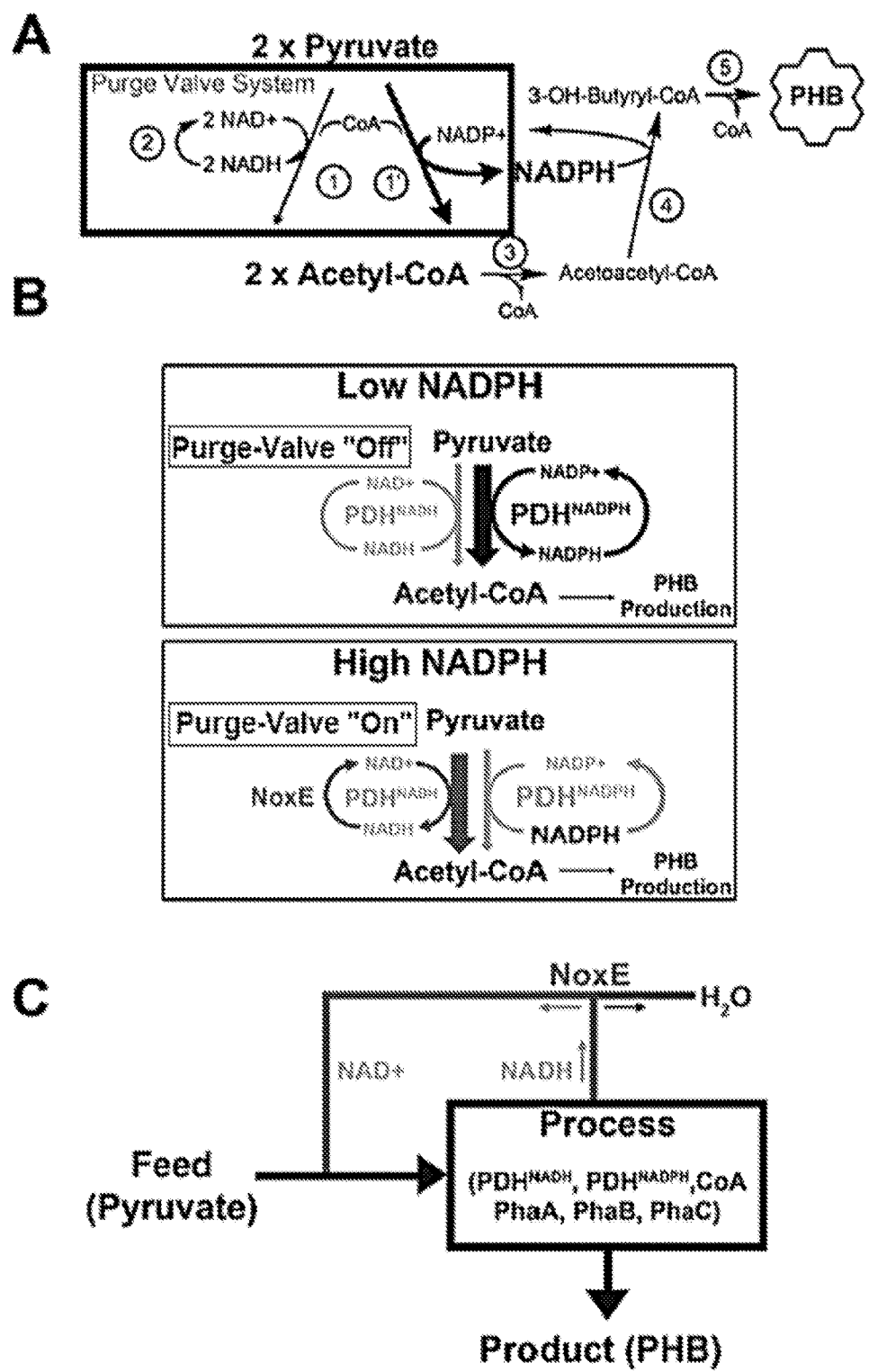
FIGS. 1A-C shows a synthetic biochemistry purge valve system for the production of PHB. (A) The in vitro metabolic pathway for the conversion of pyruvate to PHB. The pathway comprises 6 separate reactions: reaction 1 ($PDH^{NADH}$), reaction 2 ($PDH^{NADPH}$), reaction 3 (NoxE), reaction 4 (PhaA), reaction 5 (PhaB), reaction 6 (PhaC). The purge valve is highlighted in the boxed pathway. (B) How the purge valve is designed to function. At low NADPH (high NADP+), $PDH^{NADPH}$ reaction dominates, generating Acetyl-CoA and NADPH from pyruvate and $NADP^+$. The purge valve is effectively "off". In high NADPH (low $NADP^+$) conditions, the $PHD^{NADPH}$ enzyme is starved for oxidized cofactor, shutting down the pathway to Acetyl-CoA. In this situation, the $PDH^{NADH}$/NoXE system takes over, producing Acetyl-CoA; the purge valve is "on". (C) An exemplary chemical engineering schematic of the purge valve system used in the production of PHB from pyruvate, involving a cofactor recycle loop.

As used herein and in the appended claims, the singular forms "a," "and," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides in vitro biosynthetic pathways comprising a metabolic purge vale as well as providing recombinant microorganism having a metabolically engineered pathway comprising a metabolic purge valve for the production of a desired product or intermediate.

As used herein a "cofactor" generally refers to a chemical compound or metabolite that is required for a protein's biological activity. These proteins are commonly enzymes, and cofactors assist in biochemical transformations. Cofactors include, but are not limited to, one or more inorganic ions, or a complex organic or metalloorganic molecule sometimes referred to as a coenzyme; most of which are derived from vitamins and from required organic nutrients in small amounts. Some enzymes or enzyme complexes require several cofactors. For example, the multienzyme complex pyruvate dehydrogenase at the junction of glycolysis and the citric acid cycle requires five organic cofactors and one metal ion: loosely bound thiamine pyrophosphate (TPP), covalently bound lipoamide and flavin adenine dinucleotide (FAD), and the cosubstrates nicotinamide adenine dinucleotide ($NAD^+$) and coenzyme A (CoA), and a metal ion ($Mg^{2+}$). Organic cofactors are often vitamins or are made from vitamins. Many contain the nucleotide adenosine monophosphate (AMP) as part of their structures, such as ATP, coenzyme A, FAD, and $NAD^+$.

An "enzyme" means any substance, typically composed wholly or largely of amino acids making up a protein or polypeptide that catalyzes or promotes, more or less specifically, one or more chemical or biochemical reactions.

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., a carbohydrate, a sugar phosphate, pyruvate etc.), an intermediate in (e.g., acetyl-coA), or an end product (e.g., isoprene or PHB) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

As used herein, the term "metabolically engineered" or "metabolic engineering" involves rational pathway design and assembly of biosynthetic genes, genes associated with operons, and control elements of such polynucleotides, for the production of a desired metabolite, such as acetyl-CoA, higher alcohols or other chemical, in a microorganism or in vitro. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolic purge valve" refers to an engineered metabolic pathway that 'purges' excess metabolites and/or co-factors resulting in a recycling of the metabolite or co-factor for use in a primary metabolic pathway.

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described herein, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway as described herein. In addition, a substrate can be an oxidized or reduced co-factor or a factor that is phosphorylated or de-phosphorylated.

Metabolic engineering and synthetic biology have been employed for the production of high value chemicals but have not been as successful as hoped in meeting the stringent economics of large scale commodity chemical manufacturing. Microbial systems are often hampered by a variety of technical challenges that make it hard to achieve cost competitiveness, including poor yields due to competing pathways; low productivity caused by slow growth rates or difficulties in pathway optimization; contaminating microbial growth; product toxicity; and expensive product isolation.

One approach that is beginning to receive attention is to perform complex biochemical transformations using mixtures of enzymes in a reaction vessel or flow system rather than within a cell. Building single, dedicated pathways in vitro can eliminate side reactions that occur in the cell, so that nearly 100% yields and fast reaction times are possible. In vitro biochemical systems also allow for more precise control over optimization and product toxicity problems can be more easily diagnosed and mitigated. Moreover, product extraction can be more facile.

Traditionally, in vitro pathway construction has been relegated to use as a research tool or in applications that require only 1-3 enzymes for the production of chiral compounds and other high value chemicals. Improvements in protein expression and access to stable enzymes have made more complex systems possible. In vitro biotransformation systems have been reported in recent years involving systems of over thirty enzymes. One of the first modern studies in this area was an artificial pathway that produced hydrogen from starch. The concept was recently advanced with a creative system that generated hydrogen from cellobiose at nearly 100% yields. In another effort, hyper-thermophilic glycolysis enzymes were heterologously expressed, heat purified, and assembled to convert glucose to n-butanol in 82% yield. In another study, an elegantly simplified non-phosphorylative Entner-Doudoroff pathway from hyper-thermophilic archaea was constructed to produce ethanol and isobutanol in ~55% yields. These pioneering studies illustrate the flexibility of synthetic biochemistry and the potential for high yields.

Maintaining proper cofactor balance is an essential part of generating flux and providing a driving force through an enzymatic pathway. In vivo, the enzymatic specificity for the cofactors NADH and NADPH are typically used to control the carbon flux through catabolic and anabolic pathways respectively. Organisms typically sense the reduction state of these cofactors and use this information to up-regulate or down-regulate catabolic and anabolic pathways to cope with environmental changes. In vitro systems, however, do not have the myriad of peripheral pathways that facilitate this control. Moreover, the natural anabolic and catabolic specificities for NADH and NADPH complicate in vitro biotransformations. Synthetic biochemistry systems have often dealt with these problems by careful considerations of cofactor stoichiometry in pathway design, through the use of expensive sacrificial metabolites, reengineering enzymes so that only a single cofactor type is needed, adding excess cofactors, or constantly adding intermediates to the reaction mix to sustain the process.

Although the methods, compositions and systems described herein are described with reference to certain metabolic products, the methods, compositions and systems are applicable to a broad range of recombinant biochemical pathways were co-factor recycling is important. In one exemplary engineered pathway the disclosure describes the production of polyhydroxybutyrates (PHBs) and polyhydroxyalkanoates (PHAs). In another exemplary embodiment, the disclosure describes the production of isoprene. Both embodiments utilize a molecular purge valve system of the disclosure to maintain appropriate co-factor balance.

PHBs and other PHAs are biodegradable thermoplastics. PHAs can have characteristics similar to many popular petrochemical derived polymers, but are nontoxic and biodegradable, thus these compositions are attracting increased attention as a possible green alternative to petroleum based polymers in a wide range of applications. The best characterized and most abundant PHA polymer is polyhydroxybutyrate (PHB) that is naturally produced from Acetyl-CoA as a carbon and energy storage mechanism in many organisms. Currently, industrial production of PHB is done by in vivo batch culture processes under nutrient starvation. This process is typically very time consuming, requires large fermentation volumes, and requires expensive methods for the extraction of PHB. Prior attempts to produce bioplastic in vitro have required the addition of sacrificial substrates and a molar excess of cofactors to convert acetate to PHB.

Isoprene is a platform chemical for a variety of products, but it is mostly employed in the production of synthetic rubber. The isoprenoid pathway also provides precursors for over 25,000 known biomolecules including drugs such as taxol and potential biofuels. There have been a number of efforts to produce isoprene in microorganisms and the best reported yield is 28% from glucose. Korman et al. (Protein Sci., 23(5):576-85, May 2014), showed that a synthetic biochemistry system could produce isoprene in >95% yield from pyruvate as long as high energy cofactors were added. Examples of isoprenoids that can be produced by the methods, compositions and systems of the disclosure are selected from the group consisting of a hemiterpene, monoterpene, diterpene, triterpene, tetraterpene, sesquiterpene, and polyterpene. For example, the isoprenoid can be selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

The disclosure describes a purge valve system for cofactor balance in in vitro pathways for chemical production and in vivo systems. For example, the disclosure describes a pathway to convert pyruvate into PHB that maintains sustainable reducing cofactor balance, without the requirement for perfect stoichiometric matching of cofactor generation and usage to carbon usage. Further, the disclosure described the use of the molecular purge valve system in other pathways. For example, the disclosure demonstrates the purge valve system can be used as the basis for the production of other Acetyl-CoA derived products by applying it to the production of isoprene from pyruvate via the mevalonate pathway. Thus, the regulatory modules described herein can free us from having to perfectly balance cofactor utilization when designing synthetic biochemistry systems.

The disclosure provides a robust node of control to balance the production and consumption of cofactors such as NADPH and NADH in a self-regulating and self-balancing manner. This in vitro pathway maintains cofactor balance without requiring adherence to stoichiometry in the generation and utilization of cofactors to ensure carbon flux. In part because the system can sustain high levels of NADPH, driving the transformation to near completion, converting for example, pyruvate to either PHB or isoprene at nearly 100% of the theoretical yield. Moreover, the high yields in the system are robust to 10-fold variations in cofactor levels.

Ultimately the methods and compositions of the disclosure can be expanded to incorporate the conversion of low cost substrates such as glucose or other sugars into pyruvate, which would involve the glycolysis pathway or parts of the glycolysis pathway. Indeed a synthetic biochemistry system employing glycolysis has been demonstrated previously. Building more complex compounds from Acetyl-CoA such as fatty acids, polyketides, and other isoprenoids incorporate the use and recycling of ATP. In such instances developing a regulatory systems like the purge valve employed here, will free synthetic biochemistry system design from having to consume the high energy cofactors during the anabolic phase in perfect stoichiometric balance. Thus, the approach can help diversify the chemical targets of synthetic biochemistry.

The biotransformation of pyruvate into PHB, illustrates a basic co-factor imbalance problem that is encountered in biochemical systems. In particular, conversion of pyruvate to Acetyl-CoA by pyruvate dehydrogenase (PDH) yields one molecule of NADH. However, the three enzyme pathway (phaA, B, and C) to PHB from Acetyl-CoA utilizes only one half a molecule of NADPH per Acetyl-CoA. Thus, the canonical pathway produces an excess of reducing equivalents. Moreover, the reducing equivalents are of the wrong type (NADH rather than NADPH). The disclosure exemplifies the purge valve system in a pathway for the regulation of NAD and NADP and their reduced equivalents, shown in FIG. 1A, that can generate the correct cofactor and regulate its production.

In the design, a synthetic biochemistry "purge valve" was developed that effectively decouples the stoichiometric production of NAD(P)H from Acetyl-CoA (FIG. 1). To this end a mixture of both an NAD$^+$-utilizing wild-type PDH (PDH$^{NADH}$), a mutant PDH that utilizes NADP$^+$ (PDH$^{NADPH}$), and a water generating NADH oxidase (NoxE) that specifically oxidizes NADH, but not NADPH was utilized. By employing this metabolic node, NADPH was generated for PHB production from pyruvate, but also dissipate excess reducing equivalents in an auto-regulatory manner. As illustrated in FIG. 1B, under low NADPH, high NADP$^+$ conditions, the mutant PDH$^{NADPH}$ can operate to generate Acetyl-CoA and restore NADPH levels. Under high NADPH, low NADP$^+$ conditions, the PDH$^{NADPH}$ activity will automatically be choked off, and the wild-type PDH$^{NADH}$ will be used preferentially to produce Acetyl-CoA and NADH. In this high NADPH condition, the reducing equivalents are not needed. Because the reducing equivalents are produced in the form of NADH and not NADPH, they are eliminated by an oxidase, NoxE. The presence of NoxE ensures that NADH never builds up and the PDH$^{NADH}$ can always operate to generate carbon for the PHB pathway in the form of Acetyl-CoA. The PDH$^{NADH}$/PDH$^{NADPH}$/NoxE system acts like a purge valve that opens under conditions of high NADPH to relieve the excess reducing equivalent "pressure" (i.e. buildup of NADH) and allow carbon flux to be maintained. An engineering schematic of the purge valve system is shown in FIG. 1C.

For example, the disclosure demonstrates that to construct an in vitro system the enzymes were acquired commercially or purified, tested for activity, and mixed together in a properly selected reaction buffer. The system comprises a core set of enzymes for the "purge valve" system and a secondary set of enzyme for the synthesis of a desired chemical or biofuel. The core purge valve system can be utilized in combination with any in vitro system that converts one set of metabolites (e.g., a first carbon source) to a second metabolite (e.g., a desired chemical product), wherein the secondary metabolic pathway (e.g., the product pathway) uses or produces and excess of co-factor metabolites (e.g., produces an excess of reducing equivalents). In such instances a purge valve system can be utilized to balance the cofactors. For example, in the case of PHB and isoprene these reducing equivalents can be utilized and optimized. In one embodiment, the metabolic pathway produces an excess of a reducing equivalent that is needed for production of the desired product. For example, in Scheme 1, below, a first metabolic step produces reducing equivalents and a second metabolic step utilizes the reducing equivalents, however, the second step uses only a fraction of the reducing equivalents produced in the first step. Thus, in a closed system, the limiting factor will be the reducing equivalents.

Scheme 1

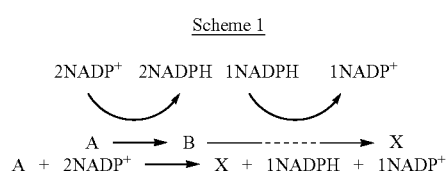

Upon utilization of the available NADP$^+$ in scheme 1, for example, the system would stop and no further metabolites ("B" or "X") would be made. However, in the purge valve system of the disclosure, a secondary pathway that can oxidize the reducing equivalents would become active and allow production of A to B, while still allowing use of the NADPH in steps B to X. Once sufficient enough NADP+ is present then the metabolic pathway from A to B would use the NADP$^+$.

In one embodiment, the purge valve for use in an in vitro system comprises: a combination of both an NADH-dehydrogenase enzyme and an NADPH-dehydrogenase and a NADH or NADPH-oxidase. In one embodiment, the purge valve system comprises an NADH-pyruvate dehydrogenase complex, an NADPH-pyruvate dehydrogenase complex and an NADH-oxidase. It should be noted that other dehydrogenase pairs can be used.

The purge valve system of the foregoing embodiment can be used in combination with any metabolic pathway that produces NADH or NADPH and utilizes a fraction of what was produced in the production of a desired product. For example, the purge system can be used in a pathway that converts pyruvate to acetyl-CoA to produce NADH or NADPH and that utilizes NADH or NADPH to further produce a desired metabolite. Exemplary pathways include the PHB and isoprene pathways described below.

The disclosure provides pathways that can be developed in vitro in a number of ways. For example, the desired enzymes can be cloned/engineered into a microorganism or cell, expressed and then purified from the culture. In another example, the enzymes can be expressed, the cells disrupted and a disrupted preparation used in the pathways of the disclosure. In another embodiment, the enzymes can be purified and tethered to a substrate in a system (e.g., in a microfluidic system) for use in the metabolic pathway. In yet another embodiment, thermophilic enzymes having the desired activity can be cloned, expressed and the cell or preparations therefrom heated to a temperature wherein the desired enzymes remain active while undesired enzymes are denatured. In yet another embodiment, the enzymes can be commercially purchased and mixed as appropriate. In all of the foregoing embodiments, the system would be combined with the necessary substrates and cofactors (e.g., $NAD^-$, $NADP^-$, $FAD^-$, AMP, ADP, ATP and the like).

Accordingly, the disclosure provides "engineered" or "modified" microorganisms that are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. The genetic material introduced into the parental microorganism contains gene(s), or parts of gene(s), coding for one or more of the enzymes involved in a biosynthetic pathway and include gene(s), or parts of gene(s), coding for one or more of the enzymes involved in a metabolic purge valve, the pathway(s) useful for the production of a desired metabolite (e.g., acetyl-phosphate and/or acetyl-CoA), and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products). For example, it may be desirable to engineer an organism to express a desired set for enzymes in a metabolic pathway while eliminating enzymes of competing pathways. This engineering can be applicable for both in vitro (where upon disruption or purification undesirable enzymes are not present) or in vivo.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a NADH-pyruvate dehydrogenase. This microorganism can act as a parental microorganism in the generation of a microorganism modified to express or over-express a second target enzyme e.g., a NADH-oxidase. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules in to the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells.

The sequence listing appended hereto provide exemplary polynucleotide sequences encoding polypeptides useful in the methods described herein. It is understood that the addition of sequences which do not alter the encoded activity of a nucleic acid molecule, such as the addition of a non-functional or non-coding sequence (e.g., polyHIS tags), is a conservative variation of the basic nucleic acid.

It is understood that a polynucleotide described above include "genes" and that the nucleic acid molecules described above include "vectors" or "plasmids." Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

In certain embodiments, a metabolic pathway converts a carbon source to a desired intermediate or end product. For example, a carbon source can be converted to pyruvate, which can be metabolized to acetyl-CoA to PHB or isoprene. Suitable carbon sources can be sugars. For example, a carbon source can be a biomass derived sugar. A "biomass derived sugar" includes, but is not limited to, molecules such as glucose, sucrose, mannose, xylose, and arabinose. The term biomass derived sugar encompasses suitable carbon substrates of 1 to 7 carbons ordinarily used by microorganisms, such as 3-7 carbon sugars, including but not limited to glucose, lactose, sorbose, fructose, idose, galactose and mannose all in either D or L form, or a combination of 3-7 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, and lignin can be generally treated by a variety of chemical, mechanical and enzymatic means to release primarily hexose and pentose sugars. These sugars can then be "fed" into a pathway to produce pyruvate as further described herein.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are known in the art.

It is understood that a range of microorganisms can be engineered to express one or more enzymes of the disclosure. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus,* Staphylococci, Streptococci, Mycoplasmas); (2) Proteobacteria, e.g., Purple photosynthetic +non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) *Radioresistant micrococci* and relatives; and (11) *Thermotoga* and *Thermosipho thermophiles.*

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces.*

Accordingly, the disclosure provides an in vitro or in vivo engineered pathway that comprises an NADPH-dehydrogenase (e.g., an NADPH-PDH or homolog thereof), an NADH-dehydrogenase (e.g., an NADPH-PDH or homolog thereof), and an NADH-oxidase (e.g., an NOX or homolog thereof).

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Materials.

Miller LB media or Miller LB-agar (BD Difco) was used for growth of bacterial strains in liquid or solid media. E. coli BL21Gold(DE3) [B, F–, ompT, hsdS$_B$, (r$_B$–,m$_B$–), dcm+, Tetr, galλ, (DE3) endA Hte] (Agilent) was used as host for both cloning and expression of recombinant proteins using pET vectors. E. coli TOP10(DE3) [F– mcrA Δ(mrr-hsdRMS-mcrBC) φ80lacZΔM15 ΔlacX74 nupG recA1 araD139 Δ (ara-leu)7697 galE15 galK16 rpsL(Str$^R$) endA1 λ$^–$] was used for expression of recombinant proteins from the pBAD/p15A vector. Plasmids pET28a(+) and pET22b(+) were purchased from Novagen. HotStart Taq Mastermix (Denville) was used for gene amplification from genomic or plasmid DNA. Phusion DNA polymerase (Finnizymes), Taq DNA ligase (MCLab), and T5 Exonuclease (Epicenter) were purchased separately and used to make the assembly master mix (AMM) used for cloning. ATP, (±)-α-lipoic acid, pyruvate, Coenzyme A, and NAD$^+$ were from Sigma.

Plasmid Construction.

The expression plasmids for the PHB enzymes were constructed from the pET28a plasmid backbone using the Nde1 and Sac1 cut sites to produce constructs with an N-terminal 6×His tag for purification. The genes encoding acetyl CoA acetyltransferase (phaA; YP_725941, the information associated with the accession number is incorporated herein by reference) and acetoacetyl-CoA reductase (phaB; YP_725942, the information associated with the accession number is incorporated herein by reference) were amplified and cloned from R. eutropha genomic DNA. The gene encoding polyhydroxybutyrate synthase (phaC; HE_610111, the information associated with the accession number is incorporated herein by reference) was synthesized and codon optimized for expression in an E. coli host before being subcloned into the pET28a expression vector. For the isoprene pathway, the constructs were the same as described in reference (Korman, T. P., Sahachartsiri, B., Li, D., Vinokur, J. M., Eisenberg, D. and Bowie, J. U. (2014), "A synthetic biochemistry system for the in vitro production of isoprene from glycolysis intermediates." Protein Science. doi: 10.1002/pro.2436).

E. coli BL21-Gold cells were used as the host strain for enzyme expression. All enzymes were expressed in Luria-Bertani (LB) media supplemented with 50 μg/mL kanamycin and were induced with 0.2 mM isopropyl-β-D-1-thioglactopyranoside added to the culture at the end of log phase growth. The phaA, phaB, MVK, PMVK, and IspS were induced at 37° C. overnight and phaB, THL/HMGR, HMGS, and IDI were induced at 18° C. overnight. The phaC was induced at 25° C. for 5 hours before harvesting.

Enzyme Purification.

Cells from 0.5 L of culture were harvested by centrifugation and resuspended in 150 mM Tris pH 7.5, 100 mM NaCl. The cells were lysed on ice with sonication and the cell debris was removed by 12,000×g centrifugation at 4° C. The supernatant was then mixed with 5 mL nickel-nitrilotriacetic acid (NTA) agarose and after 30 minutes, the agarose slurry was loaded onto a gravity column and washed with five column volumes of 100 mM Tris pH 7.5, 100 mM NaCl, 15 mM imidazole. The enzyme was then eluted with 250 mM imidazole, 100 mM Tris pH 7.5. The resulting enzyme was dialyzed into 50 mM Tris pH 7.5, 50 mM NaCl and stored at 4° C.

Expression Vectors for PDH Subunits E1αβ, E2, and E3, and E. coli LplA.

The E1, E2, and E3 domains were all amplified separately from G. stearothermophilus genomic DNA (ATCC) using primers that contained 15-20 bp complementary to the gene and 15-20 bp complementary to the multiple cloning site in the vector where the gene would be placed. The genes encoding E1α and E1β were amplified together from G. stearothermophilus genomic DNA and cloned into pET28a(+) that had been digested with NcoI and XhoI. This created a tag-less construct for E1 expression under control of the T7 promoter where E1α translation uses the RBS from the pET28 vector while E1β uses the endogenous RBS from G. stearothermophilus. The E2 and E3 domains were amplified separately and cloned into pET22b(+) digested with NdeI and XhoI or pET28a(+) digested with NcoI and XhoI respectively to create tag-less E2 and E3 constructs. The E. coli lipoate protein ligase, LplA, was amplified from E. coli K12 genomic DNA and assembled into pBAD/p15A digested with XhoI and EcoRI to create 6×His-LplA.

Overexpression and Purification of G. sterothermophilus PDH Subunits and E. coli LplA.

All E. coli strains were grown at 37° C. in LB-media supplemented with appropriate antibiotic (100 μg/mL ampicillin, 50 μg/mL kanamycin, or 34 μg/mL chloramphenicol). For all constructs, 5 mL of overnight starter culture was used to inoculate 1 L of LB-media. Once the OD$_{600}$ reached 0.6, 0.3 mM IPTG (pET vectors) or 0.02% arabinose (pBAD/p15A) was added to induce protein expression. After 16 hours, cells were harvested, resuspended (4 mL/g wet cells) in 50 mM Tris-Cl pH 7.5, 0.1M NaCl (Buffer A), lysed by sonication, and cell debris removed by centrifugation at 30,000×g for 20 min.

25 mL of the E. coli lysate containing 6×His-LplA was loaded onto a 3 mL Ni-NTA resin (Qiagen), washed with 25 mL Buffer A containing 10 mM imidazole, and eluted with 5 mL Buffer A containing 250 mM imidazole. Pure 6×His-LplA was then stored at 4° C. until use.

The individual domains of G. stearothermophilus PDH were partially purified from E. coli lysates by heat prior to modification and reconstitution of the PDH complex. E1αβ, E2, or E3 containing lysates were incubated at 65° C. for 35 minutes to heat denature E. coli proteins followed by centrifugation at 30,000×g for 20 min to pellet the precipitated proteins. Nearly all of the PDH domains remain in the supernatant. Next, the E2 domain was lipoated in the heated extract by the addition of 1 mM (±)-α-lipoic acid, 2 mM ATP, 3 mM MgCl$_2$, and 50 μg of purified 6×His-LplA. The lipoation reaction was then allowed to proceed with gentle mixing overnight at 25° C., yielding lipoated E2 (E2lip). After lipoation, E1αβ, E2lip, and E3 were mixed in a 3:1:3 molar ratio and incubated for at least 1 hour at 25° C. to form the active GsPDH complex. The GsPDH complex was then isolated by ultracentrifugation (Beckman) for 4 hours at 95,000×g. The resulting yellow pellet was resuspended in 20 mM Tris-Cl, pH 7.5 in 1/50 the starting volume and assayed for activity. SDS-PAGE analysis confirmed the presence of all 4 domains and indicated that the preparation was >90% pure. The reconstituted complex was stored at 4° C. until use.

Enzyme Activity and Optimization.

NoxE was assayed by monitoring the oxidation of NAD(P)H at 340 nm. The assay was carried out in 100 mM tris-HCl pH 7.5, 5 mM MgCl$_2$, 5 mM KCl, and 0.2 mM NAD(P)H.

WT and mutant PDH were assayed by monitoring the reduction of NAD(P)$^+$ at 340 nm. The assay was carried out in 50 mM Tris pH 7.5, 5 mM MgCl$_2$, 5 mM pyruvate, 1 mM CoA, and 0.5 mM of NAD(P)$^+$.

PhaC was assayed by monitoring the absorbance of the hydrolysis of the thioester bond of the substrate 3HBCoA at 235 nm. The assay was carried out in 100 mM Tris pH 7.5, 5 mM MgCl$_2$ and 0.15 mM 3HBCoA.

Activity of isoprene pathway enzymes were measured as reported previously (Korman et al.). The amount of each enzyme in the reconstituted isoprene pathway described below is show in Table A.

TABLE A

List of the enzymes and activities used in the production of PHB or Isoprene from pyruvate.

| | Enzyme | Units/mg | mg added | Units added |
|---|---|---|---|---|
| 1 | GsPDH$^{NAD}$ | 0.082 ± 0.007 | 0.002/0.0013 | 0.00016/0.00011 |
| 1' | GsPDH$^{NADP}$ | 0.12 ± 0.008 | 0.076/0.0095 | 0.009/0.001 |
| 2 | NoxE | 0.35 ± 0.036 | 0.020/0.00625 | 0.007/0.0022 |
| 3 | PhaA | 76.2 ± 4.4 | 0.023 | 1.75 |
| 4 | PhaB | 6.1 ± 0.6 | 0.014 | 0.085 |
| 5 | PhaC | 142.7 | 0.032 | 4.57 |
| 6 | EfTHL-HMGR | 0.06 ± 0.002[a] | 0.003 | 0.00018 |
| 7 | EfHMGS[b] | 0.6 ± 0.01 | 0.041 | 0.025 |
| 8 | EfHMGR | 0.06 ± 0.002[a] | 0.023 | 0.0014 |
| 9 | ScMVK | 47.0 ± 0.9 | 0.008 | 0.38 |
| 10 | SsPMVK | 0.8 ± 0.02 | 0.029 | 0.023 |
| 11 | ScMDC | 4.0 ± .07 | 0.038 | 0.152 |
| 12 | EcIDI | 0.035[c] | 0.083 | 0.003 |
| 13 | PalspS | 0.156[d] | 0.088 | 0.014 |

[a]Assayed in forward direction (synthesis) by coupling to MvaS and monitoring NADPH consumption Final PHB Reaction Conditions and Analysis.

The optimized self-sustaining reaction for the biotransformation of pyruvate to PHB was composed of 250 mM Tris pH 7.5, 5 mM MgCl, 5 mM KCl, 0.5 mM CoA, 0.1 mM NAD$^+$, 0.5 mM NADP$^+$, 50 mM pyruvate, 2 μg PDH$^{NADH}$, 76 μg PDH$^{NADPH}$, 23 μg phaA, 14 μg phaB, and 32 μg phaC in a final reaction volume of 200 μL. The reactions were initiated with the addition of pyruvate, which was left out of the initial mixture. All PHB reactions were performed at room temperature. For testing the autoregulatory behavior of the purge valve, some enzyme concentrations were suboptimal: 5 μg phaA, 2.5 μg phaB, and 1.9 μg phaC.

To assay for PHB, the reactions were lyophilized and incubated with 1 mL chloroform, 0.45 mL methanol, and 0.05 mL H$_2$SO$_4$ to hydrolyze the polymer and generate methyl 3-hydroxybutyrate. The reactions were extracted with 0.5 ml water and 1 μL of the chloroform layer was applied to a 0.25 micron HP-Innowax column using a HP 5890 Series II gas chromatogram. The GC method used an injection temperature that was held at 35° C. for 5 minutes before it was increased to 275° C. over 40 minutes. The peak intensities were compared to an authentic standard to assess concentrations.

Isoprene Reaction Conditions and Analysis.

In vitro production of isoprene was performed as described previously (Korman et al.) with the following changes. 200 μL reactions were set up in 2 mL gas tight vials containing enzymes, 3 mM pyruvate, 15 mM ATP, 0.6 mM CoA, 0.2 mM NAD+, 0.4 mM NADP+(or 5 mM NADPH), 10 mM MgCl$_2$, 20 mM KCl, 0.1 mM thiamine pyrophosphate in 100 mM tris-Cl pH 8.5 and incubated at 32° C. for 18 hours. Isoprene production was monitored by direct sampling of 100 μL the headspace using a 100 μL gas-tight syringe. The headspace was analyzed by GC-FID (HP5980II) equipped with a GS-GasPro column (0.32 mm×30 m, Agilent). The amount of isoprene produced was quantified by comparison to a standard curve of various isoprene concentrations sampled in the same manner.

To implement the purge valve module, an NADP$^+$-utilizing PDH was needed. A mutant of E. coli PDH has been engineered to have NADP$^+$ specificity by introducing mutations into the E3 enzyme (EcE3). The E. coli PDH was, however, unstable. A mutant of the thermophilic G. stearothermophilus PDH was engineered that preferentially accepts NADP$^+$ with increased enzyme stability.

Figure 2:
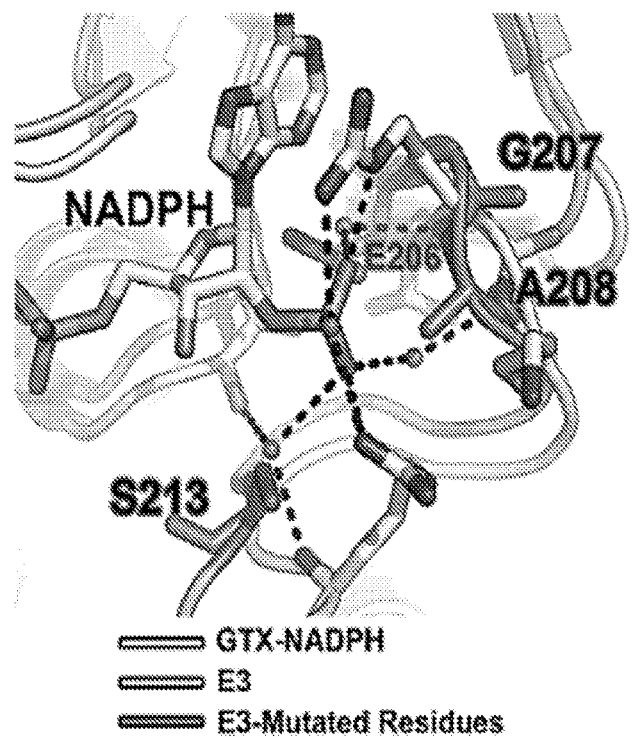
FIG. 2 shows the design of the $PDH^{NADPH}$ enzyme. The structures of the wild type G. stearothermophilus E3 subunit (E3, backbone trace) is shown overlaid on the structure of E. coli glutathione reductase (GTX-NADPH, gray backbone trace). The NADPH substrate from glutathione reductase is shown in stick representation, showing the placement of the phosphate moiety that needs to be accommodated. The residues changed to accept the phosphate (E206V, G207R, A208K, and S213R) are shown.

Similar to design of the E. coli PDH mutant, the G. stearothermophilus PDH mutant (SEQ ID NO:7) was designed by overlaying the known structure of the G. stearothermophilus E3 subunit (GsE3) with the known structure of the related E. coli glutathione reductase, which utilizes NADP$^+$. The structural superposition allowed for positioning the additional phosphate moiety in the active site of the GsE3, based on how it was placed in glutathione reductase (see FIG. 2). The side chain substitutions were then designed in GsE3 that might allow acceptance of the phosphate. Guidance was identified from a prior successful design of the EcE3 enzyme which shares 47% sequence identity with the GsE3. The mutations introduced into EcE3 were E206V, G207R, A208K, G209H and S213R (GsE3 numbering). After examining the changes in the context of the GsE3 structure, all were introduced but G209H, because it appeared that the new His side chain might create steric clashes with nearby K224 and N237 residues.

The kinetic properties of the engineered and wild-type enzymes reveal that the mutations alter specificity as desired. The kinetic parameters are listed in Table B. For the wild-type G. stearothermophilus enzyme (GsPDH$^{NADH}$), $k_{cat}$ is 11.2 times higher with NAD+ than NADP+ and $k_{cat}/K_m$ is 1150 times higher. For the engineered mutant (GsPDH$^{NADPH}$), $k_{cat}$ is 7.3 times higher with NADP+ than NAD+ and $k_{cat}/K_m$ is 21 times higher. Thus, we were able to flip the specificity of the PDH enzyme.

TABLE B

List of the catalytic properties of the purge valve enzymes.

| Enzyme Name | Substrate | $K_m$ (mM) | $k_{cat}$ (µM/min/mg) | $k_{cat}/K_m$ |
|---|---|---|---|---|
| GsPDH-NAD+ | NAD+ | 0.013381 ± 0.00083 | 82.651 ± 0.66 | 6167.91 |
|  | NADP+ | 1.381 ± 0.41 | 7.3954 ± 0.85 | 5.36 |
|  | Pyruvate | 0.52736 ± 0.049 | 91.976 ± 1.9 | 174.40 |
| GsPDH-NADP | NADP+ | 0.157 ± 0.013 | 117.75 ± 8.1 | 750.00 |
|  | NAD+ | 0.45269 ± 0.178 | 16.104 ± 1.8 | 35.56 |
|  | Pyruvate | 0.42328 ± 0.068 | 174.3 ± 2.7 | 411.76 |
| NoxE | NADH | 0.074925 ± 0.026 | 348.57 ± 36.5 | 4653.81 |
|  | NADPH | 2.9515 ± 0.77 | 1.4009 ± 0.32 | 0.47 |

Figure 7:
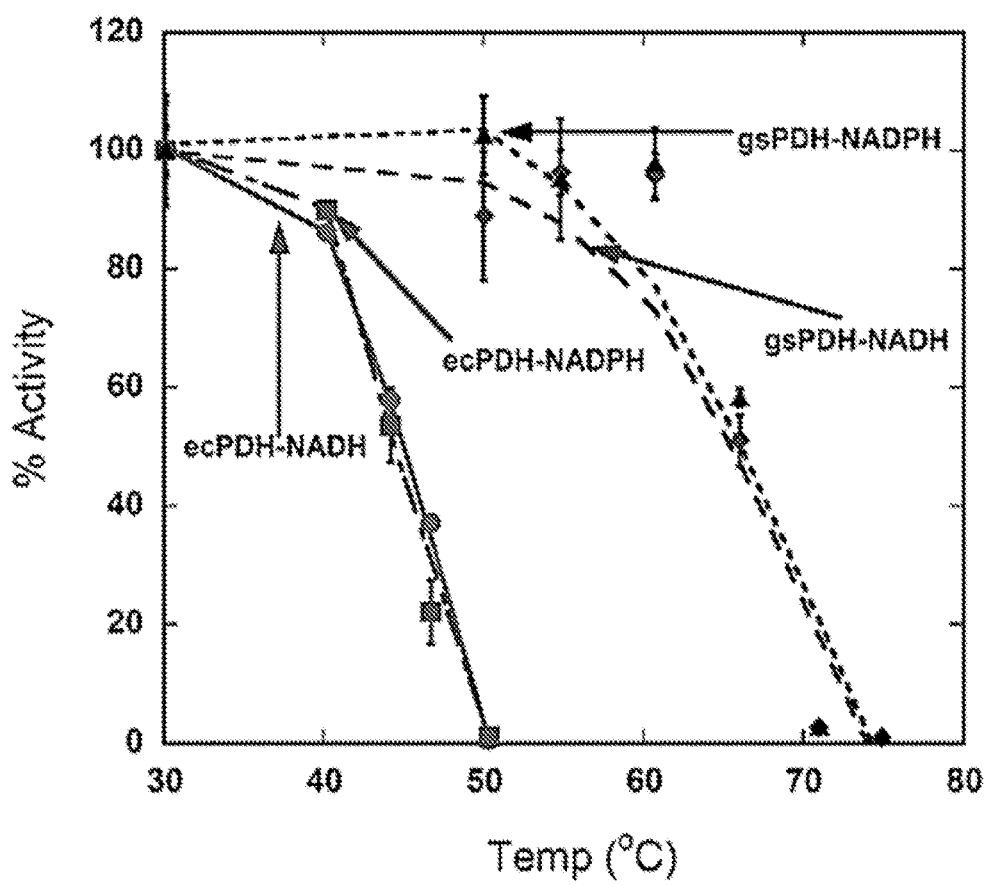
FIG. 7 shows the stability of the GsPDH enzymes. Enzymes were incubated at a given temperature for 1 hour and then immediately assayed for activity.

The GsPDH$^{NADH}$ and GsPDH$^{NADPH}$ enzymes (henceforth designated PDH$^{NADH}$ and PDH$^{NADPH}$) were much more stable than their *E. coli* counterparts. As shown in FIG. 7, the *G stearothermophilus* enzymes retained ~50% activity after one hour incubation at 67° C. whereas the *E. coli* PDH enzymes were completely inactivated at 50° C.

A second aspect of the purge valve design is the use of an NADH oxidase with high cofactor specificity. NoxE from *L. lactis* was selected as it is a water forming NADH oxidase so it doesn't generate any toxic products such as hydrogen peroxide. As shown in Table B, the $K_{cat}$ of NoxE is 248.8 times greater with NADH than NADPH and $k_{cat}/K_m$ is 9900 times greater.

The enzymes chosen for the various experiments are listed in Table C. In the initial tests only the wild type, PDH$^{NADH}$ complex and NoxE was used to generate Acetyl-CoA and NADPH was supplied exogenously. After optimizing enzyme ratios in this system, the mutant PDH$^{NADPH}$ was added to test in situ generation of NADPH. Finally, the amount of PDH$^{NADPH}$ was optimized, keeping the other enzymes fixed.

|  | Enzyme | Name | Accession Number | Plasmid | Tag | Organism |
|---|---|---|---|---|---|---|
| Purge Valve ||||||||
| 1 | PDH$^{NADH}$ | Pyruvate Dehydrogenase Complex |  |  |  | *G. stearothermophilus* |
| 1' | PDH$^{NADPH}$ |  |  |  |  |  |
| 1a | E1a | Pyruvate Dehydrogenase Subunit a | P21873 (SEQ ID NO: 1) | pET28 | none | *G. stearothermophilus* |
| 1b | E1b | Pyruvate Dehydrogenase Subunit b | P21874 (SEQ ID NO: 2) | pET28 | none | *G. stearothermophilus* |
| 1c | E2 | Dihydrolipoamide Acetyltransferase | CAA37630 (SEQ ID NO: 3) | pET22 | none | *G. stearothermophilus* |
| 1d | E3$^{NADH}$ | Dihydrolipoamide Dehydrogenase | P11959 (SEQ ID NO: 5) | pET28 | none | *G. stearothermophilus* |
| 1'd | E3$^{NADPH}$ | Mutant Dihydrolipoamide Dehydrogenase | P11959 (SEQ ID NO: 7) | pET29 | none | *G. stearothermophilus* |
| 1e | LplA | Lipoate Protein Ligase | NP_418803 (SEQ ID NO: 8) | pBAD/p15A | N-His | *E. coli* |
| 2 | NoxE | NADH oxidase (H20 forming) | YP_007507681 (SEQ ID NO: 10) | pET22 | C-His | *L. lactis* |
| PHB Pathway ||||||||
| 3 | PhaA | Acetyl-CoA acetyltransferase | GJUJ-1435 (SEQ ID NO: 11) | pET28 | N-His | *R. eutropha* |
| 4 | PhaB | 3-hydroxybutryl-CoA reductase | GJUJ-1436 (SEQ ID NO: 12) | pET28 | N-His | *R. eutropha* |
| 5 | PhaC | Polyhydroxybutyrate synthase | G8BLJ2 (SEQ ID NO: 13) | pET28 | N-His | *C. necator* sp. S-6 |
| Isoprene Pathway ||||||||
| 6 | THL/HMGR | Thiolase/HMG-CoA Reductase fusion | WP_002357755 (SEQ ID NO: 14) | pET28 | N-His | *E. faecalis* |
| 7 | HMGS | HMG-CoA Synthase A110G Mutant | WP_010785222 (SEQ ID NO: 15) | pET28 | N-His | *E. faecalis* |
| 8 | HMGR | HMG-CoA Reductase | WP_002357755 (SEQ ID NO: 16) | pET28 | N-His | *E. faecalis* |
| 9 | MVK | mevalonate kinase | BAA24409 (SEQ ID NO: 17) | pET28 | N-His | *C. cerevisiae* |
| 10 | PMVK | phosphomevalonate kinase | NP_344303 (SEQ ID NO: 18) | pET28 | N-His | *S. solfataricus* |
| 11 | MDC | diphosphomevalonate decarboxylase | NP_014441 (SEQ ID NO: 19) | pET28 | N-His | *S. cerevisiae* |
| 12 | Idi | isopentenyl diphosphate isomerase | NP_417365 (SEQ ID NO: 20) | pET22 | C-His | *E. coli* |
| 13 | IspS | Isoprene Synthase | Q50L36 (SEQ ID NO: 21) | pET28 | N-His | *P. alba* |

The sequences associated with the foregoing accession numbers are incorporated herein by reference. The SEQ ID NOs set forth above provide the polypeptide sequences. The coding sequences are readily available to one of skill in the art.

Figure 3:
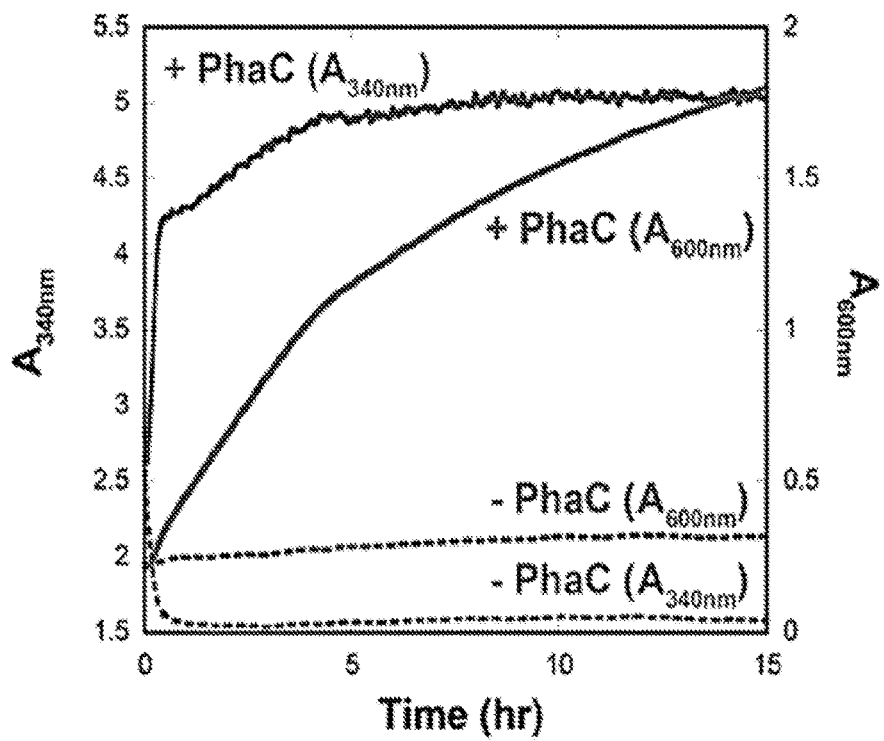
FIG. 3 shows the production of PHB using an optimized system. In this reaction the production of PHB is monitored by an increase $A_{600}$ caused by precipitation of the PHB granules. No increase is seen in the absence of the PHB polymerase, PhaC. The production of PHB is confirmed by a gas chromatography assay. The $A_{340}$ monitors the level of NADPH because no NADH is allowed to build up because of the presence of NoxE. The purge valve system maintains a high level of NADPH throughout the reaction.

The progress of the optimized pyruvate to PHB reaction is shown in FIG. 3 along with a control lacking the last enzyme, phaC. Both reactions had a PDH$^{NADPH}$:PDH$^{NADH}$ ratio of 40:1. At this ratio, the NADPH levels rise rapidly ($A_{340}$) and are maintained throughout the time course (NoxE rapidly oxidizes NADH so changes in $A_{340}$ reflect only changes in NADPH levels). At the same time, PHB granules are produced as monitored by $A_{600}{}^{36}$.

PHB production was assayed using a gas chromatography method and found that the optimized reaction produced 2.45±0.5 mg/mL of PHB from 50 mM pyruvate which represents nearly complete conversion (94±20%) of pyruvate to plastic. In the optimized system, 0.5 mM NADP$^+$ were initially used, so achieving 94% yield requires over 90 turnovers of the NADP$^+$ cofactor, indicating a high level of system sustainability.

Figure 8:
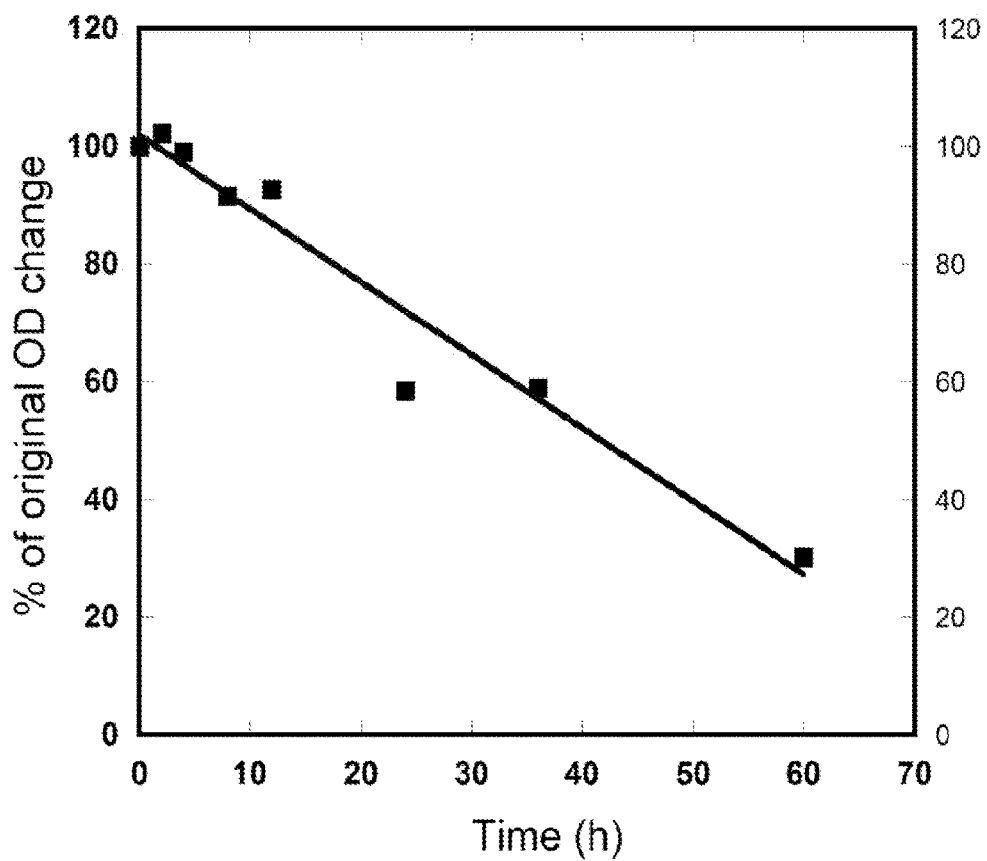
FIG. 8 shows the stability of the PHB system at room temperature. All the components of the optimized PHB system were mixed, leaving out pyruvate and then the system was incubated at room temperature. At various times the reaction was initiated by the addition of pyruvate and the extent of the reaction monitored by the final $OD_{600}$. The plot shows the percent extent of reaction achieved for each pre-incubation time.

The stability of the full system was assessed by mixing components together and then initiating the reaction at various time delays. The decrease in extent of the reaction is shown in FIG. 8. The extent of reaction remains ~50% after two days.

Figure 4:
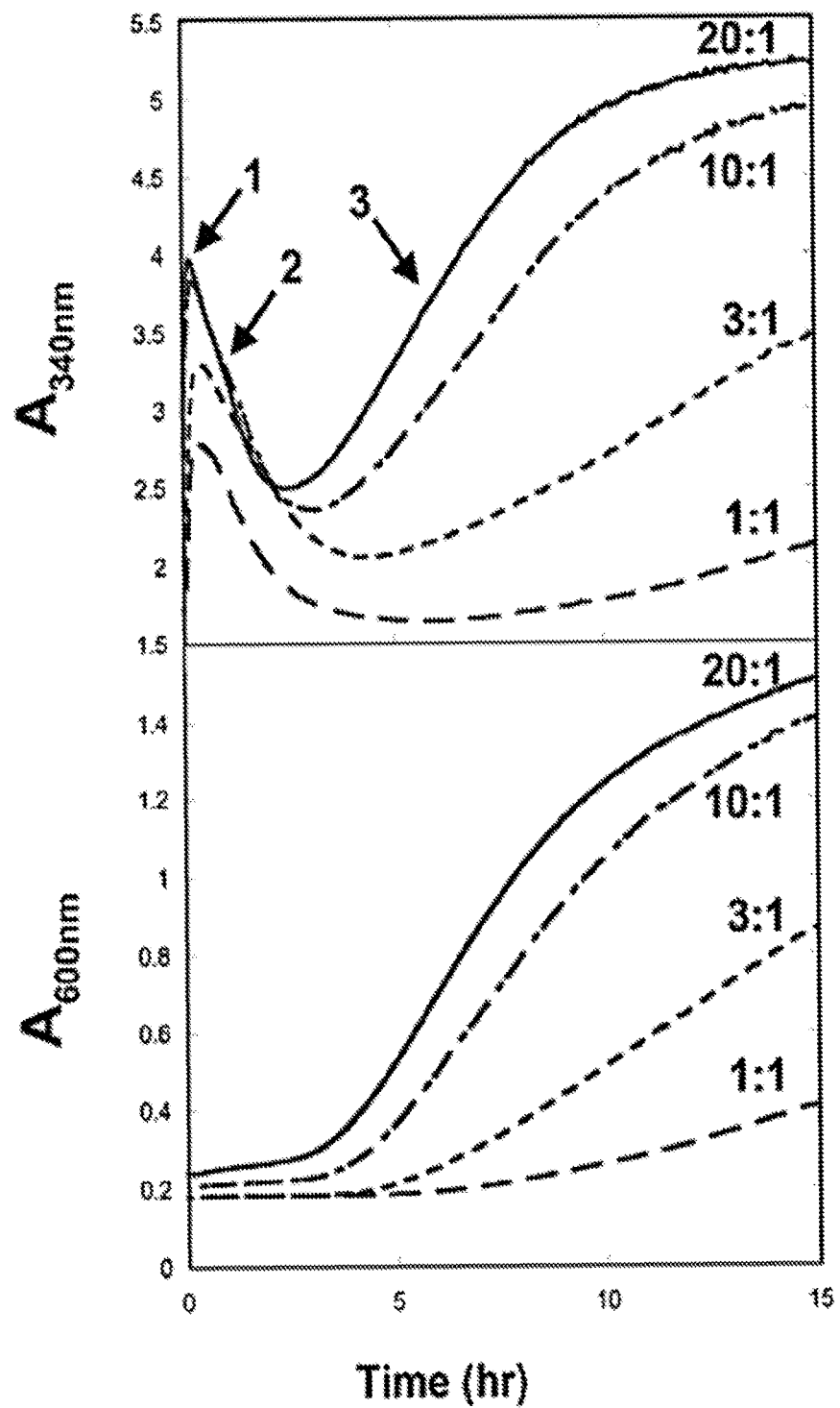
FIG. 4 shows a time course of pyruvate to PHB optimization reaction using sub-optimal ratios of $PDH^{NADPH}$ and $PDH^{NADH}$. The $A_{340}$ traces, monitoring NADPH levels fall into three distinct phases. A fast initial reduction of NADPH by the $PDH^{NADPH}$ is followed by a slow oxidation of NADPH by PhaB as the intermediate levels rise. As the reaction proceeds, the purge valve turns off and NADPH levels rise again. The evolution of the system coincides with the increase at $A_{600}$ which represents the precipitation of the PHB granules from solution.
Figure 5:
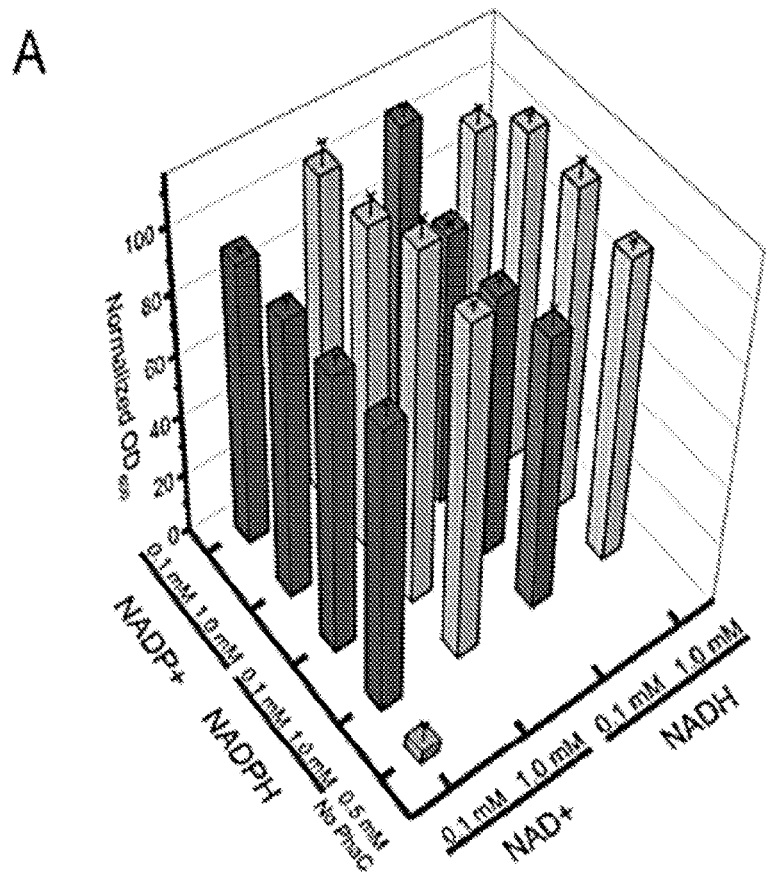
FIG. 5A-B shows the purge valve system is robust. (A) The graph shows relative yield of PHB upon starting with different amounts of each of the cofactors. The relative yields represent the ratio of the final $A_{600}$ for the reaction, relative to the final $A_{600}$ for the optimized reaction. All reactions show a relatively robust yield in comparison to the negative control lacking the final phaC enzyme (orange bar). The error bars reflect the standard deviation of three independent reactions. (B) Table of the numbers reflected in the graph in part A.

The regulatory behavior of the purge valve is better seen at sub-optimal enzyme concentrations and ratios of PDH$^{NADPH}$ to PDH$^{NADH}$ that slow down the response time. In the optimized assay (40:1 mole ratio of PDH$^{NADPH}$: PDH$^{NADH}$), a rapid rise in NADPH levels was observed, which was sustained throughout. In the non-optimal systems shown in FIG. 4, the purge valve cannot respond as rapidly to drops in NADPH concentrations so variations in NADPH levels were observed as the system develops. We still observe a rapid initial rise in NADPH levels, but as intermediates build up, the consumption starts to outstrip NADPH production. Eventually, the system compensates by generating higher levels of NADPH.

To test whether the system was robust to changes in cofactor levels, the initial cofactor concentrations were varied in the reactions and the yields of PHB were measured. Each reaction was constructed with combinations of NAD$^+$, NADH, NADP$^+$ or NADPH at either 0.1 mM or 1 mM and the production of PHB was monitored by the final OD at 600 nm. All of the reaction conditions were compared to the optimized reaction that produced nearly complete conversion of pyruvate to PHB and were within random variation. This result indicates that the purge valve can compensate readily for changes in cofactor concentrations and reduction states.

To test the versatility of the molecular purge valve and whether it can be applied as a general platform for the production of a diverse array Acetyl-CoA derived compounds the PDH purge valve was used to produce isoprene via the Acetyl-CoA dependent mevalonate pathway. Korman et al. previously described the in vitro production of isoprene from pyruvate, which required the use of exogenously added NADPH. Similar to the PHB pathway the mevalonate pathway has an inherently different carbon and cofactor stoichiometry. In particular, the mevalonate pathway requires 3 Acetyl-CoA and 2 NADPH for the production of isoprene (see FIG. 6A). Thus, system sustainability requires generation and regulation of NADPH levels.

Figure 6:
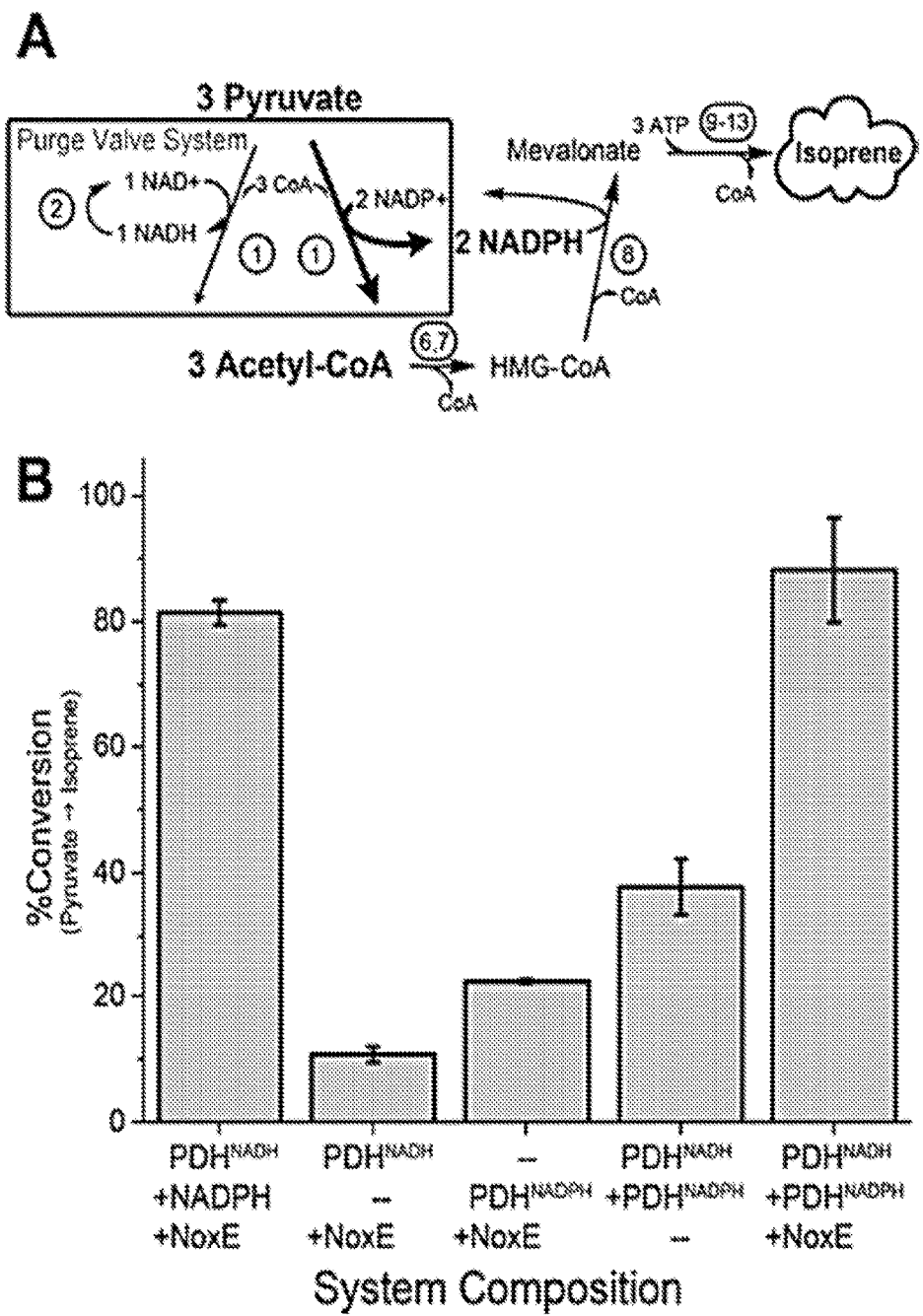
FIG. 6A-B shows employment of the purge valve for the production of isoprene. (A) The in vitro metabolic pathway for the conversion of pyruvate to isoprene. The purge valve highlighted in the box comprising the same enzymes/reactions as in FIG. 1A. In the mevalonate pathway, 3 Acetyl-CoA are used to make HMG-CoA (enzymes 6 and 7). HMG-CoA is reduced by HMGR (enzyme 8) with 2 NADPH to give mevalonate. 3 ATP are then used to convert mevalonate to isopentenyl pyrophosphate followed by production of isoprene (enzymes 9-12). (B) The graph shows the dependence of isoprene production on the purge valve. No purge valve was used in the first reaction ($PDH^{NADH}$, NADPH, NoxE). NADPH was simply added and NADH recycled using NoxE. The final experiment ($PDH^{NADH}$, $PDH^{NADPH}$, NoxE) shows results employing the full purge valve system. Leaving out any component of the purge valve system resulted in dramatic decreases in isoprene production. Each reaction was performed in duplicate.

Experiments were performed to test whether the purge valve system can replace exogenously added NADPH in the production of isoprene. As shown in FIG. 6B, the full purge valve system produces an 88.2±8.4% yield from 3 mM pyruvate. This yield is even higher than the 81.4±2.0% yield obtained if we add NADPH exogenously (FIG. 6B). If any of the purge valve components (PDH$^{NADPH}$, PDH$^{NADH}$ or NoxE) were left, yields are dramatically reduced. Thus, the purge valve system is transportable to other synthetic biochemistry systems.

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant, artificial or engineered metabolic pathway comprising a plurality of enzymatic steps that converts a substrate to a product, wherein the pathway produces an unbalanced production and utilization of a cofactor, said pathway comprising:
   a first cofactor-dependent enzyme that is capable of converting a first substrate to a second substrate, said enzyme producing the unbalanced production and utilization of a cofactor;
   a second cofactor-dependent enzyme that is also capable of converting the first substrate to a second substrate, wherein the second cofactor-dependent enzyme is the first cofactor dependent enzyme having its cofactor preference altered; and
   an enzyme that recycles the cofactor.

2. The recombinant, artificial or engineered pathway of claim 1, wherein the co-factor is an oxidizing/reducing co-factor.

3. The recombinant, artificial or engineered pathway of claim 2, wherein the oxidizing/reducing co-factor is selected from the group consisting of NAD$^+$/NADH, NADP$^+$/NADPH and FAD$^+$/FADH.

4. The recombinant, artificial or engineered pathway of claim 1, wherein the cofactor comprises NAD$^+$/NADH and the second cofactor-dependent enzyme metabolizes NADP$^+$/NADPH.

5. The recombinant, artificial or engineered pathway of claim 1, wherein the first cofactor-dependent enzyme comprises a NADH dehydrogenase, and the second cofactor-dependent enzyme comprises an NADPH dehydrogenase and the enzyme that recycles the first cofactor comprises an NAD(P)H oxidase.

6. The recombinant, artificial or engineered pathway of claim 5, wherein the NADH dehydrogenase is a NADH pyruvate dehydrogenase complex.

7. The recombinant, artificial or engineered pathway of claim 6, wherein the NADH pyruvate dehydrogenase complex comprises a pyruvate dehydrogenase subunit a, a pyruvate dehydrogenase subunit b, a dihydrolipoamide acetyltransferase, and a dyhydrolipoamide dehydrogenase.

8. The recombinant, artificial or engineered pathway of claim 7, wherein the pyruvate dehydrogenase subunit a comprises a sequence that has at least 90% sequence identity to SEQ ID NO: 1, wherein the pyruvate dehydrogenase subunit b comprises a sequence that has at least 90% sequence identity to SEQ ID NO: 2, wherein the dihydrolipoamide acetyltransferase has at least 90% sequence identity to SEQ ID NO: 3, and wherein the dihydrolipoamide dehydrogenase has at least 90% sequence identity to SEQ ID NO: 5, wherein the complex converts pyruvate to acetyl-CoA.

9. The recombinant, artificial or engineered pathway of claim 7, wherein the pyruvate dehydrogenase subunit a comprises a sequence that has at least 90% sequence identity to SEQ ID NO: 1, wherein the pyruvate dehydrogenase subunit b comprises a sequence that has at least 90% sequence identity to SEQ ID NO: 2, wherein the dihydrolipoamide acetyltransferase has at least 90% sequence identity to SEQ ID NO: 3, and wherein the dihydrolipoamide dehydrogenase has at least 90% sequence identity to SEQ ID NO: 7 and preferentially uses NADP$^+$, wherein the complex converts pyruvate to acetyl-CoA.

10. The recombinant, artificial or engineered pathway of claim 5, wherein the NADPH dehydrogenase is a member of a NADPH pyruvate dehydrogenase complex.

11. The recombinant, artificial or engineered pathway of claim 10, wherein the NADPH pyruvate dehydrogenase complex comprises a pyruvate dehydrogenase subunit a, a pyruvate dehydrogenase subunit b, a dihydrolipoamide acetyltransferase, and a mutant dyhydrolipoamide dehydrogenase the preferentially uses NADP$^+$.

12. The recombinant, artificial or engineered pathway of claim 5, wherein the NAD(P)H oxidase is a NoxE or homolog thereof.

13. The recombinant, artificial or engineered pathway of claim 12, wherein the NAD(P)H oxidase comprises a sequence that has at least 50% sequence identity to SEQ ID NO: 10.

14. The recombinant, artificial or engineered pathway of claim 1, wherein the pathway is in a cell-free system.

15. The recombinant, artificial or engineered pathway of claim 1, wherein the recombinant, artificial or engineered pathway produces PHB.

16. The recombinant, artificial or engineered pathway of claim 1, wherein the recombinant, artificial or engineered pathway produces isoprene or isoprenoid compound.

17. An enzymatic system comprising a metabolic pathway including a plurality of enzymes for converting a substrate to a product, the metabolic pathway having an unbalanced utilization of reducing/oxidizing cofactors, wherein the enzymatic system comprises a metabolic purge valve comprising an NADH pyruvate dehydrogenase, and NADPH pyruvate dehydrogenase and a NADH/NADPH oxidase.

18. A recombinant polypeptide comprising a sequence that has at least 90% sequence identity to SEQ ID NO: 5 and comprising the mutations E206V, G207R, A208K, and S213R, wherein the polypeptide has dihydrolipoamide dehydrogenase activity.

* * * * *

SEQUENCE LISTING

<160> NUMBER OF SEQ ID NOS: 21

<210> SEQ ID NO 1
<211> LENGTH: 369
<212> TYPE: PRT
<213> ORGANISM: Geobacillus stearothermophilus

<400> SEQUENCE: 1

Met Gly Val Lys Thr Phe Gln Phe Pro Phe Ala Glu Gln Leu Glu Lys
1               5                   10                  15

Val Ala Glu Gln Phe Pro Thr Phe Gln Ile Leu Asn Glu Glu Gly Glu
            20                  25                  30

Val Val Asn Glu Glu Ala Met Pro Glu Leu Ser Asp Glu Gln Leu Lys
        35                  40                  45

Glu Leu Met Arg Arg Met Val Tyr Thr Arg Ile Leu Asp Gln Arg Ser
    50                  55                  60

Ile Ser Leu Asn Arg Gln Gly Arg Leu Gly Phe Tyr Ala Pro Thr Ala
65                  70                  75                  80

Gly Gln Glu Ala Ser Gln Ile Ala Ser His Phe Ala Leu Glu Lys Glu
                85                  90                  95

Asp Phe Ile Leu Pro Gly Tyr Arg Asp Val Pro Gln Ile Ile Trp His
            100                 105                 110

Gly Leu Pro Leu Tyr Gln Ala Phe Leu Phe Ser Arg Gly His Phe His

```
                115                 120                 125
Gly Asn Gln Ile Pro Glu Gly Val Asn Val Leu Pro Pro Gln Ile Ile
    130                 135                 140
Ile Gly Ala Gln Tyr Ile Gln Ala Ala Gly Val Ala Leu Gly Leu Lys
145                 150                 155                 160
Met Arg Gly Lys Lys Ala Val Ala Ile Thr Tyr Thr Gly Asp Gly Gly
                165                 170                 175
Thr Ser Gln Gly Asp Phe Tyr Glu Gly Ile Asn Phe Ala Gly Ala Phe
            180                 185                 190
Lys Ala Pro Ala Ile Phe Val Val Gln Asn Asn Arg Phe Ala Ile Ser
            195                 200                 205
Thr Pro Val Glu Lys Gln Thr Val Ala Lys Thr Leu Ala Gln Lys Ala
        210                 215                 220
Val Ala Ala Gly Ile Pro Gly Ile Gln Val Asp Gly Met Asp Pro Leu
225                 230                 235                 240
Ala Val Tyr Ala Ala Val Lys Ala Ala Arg Glu Arg Ala Ile Asn Gly
                245                 250                 255
Glu Gly Pro Thr Leu Ile Glu Thr Leu Cys Phe Arg Tyr Gly Pro His
            260                 265                 270
Thr Met Ser Gly Asp Asp Pro Thr Arg Tyr Arg Ser Lys Glu Leu Glu
        275                 280                 285
Asn Glu Trp Ala Lys Lys Asp Pro Leu Val Arg Phe Arg Lys Phe Leu
290                 295                 300
Glu Ala Lys Gly Leu Trp Ser Glu Glu Glu Asn Asn Val Ile Glu
305                 310                 315                 320
Gln Ala Lys Glu Glu Ile Lys Glu Ala Ile Lys Lys Ala Asp Glu Thr
                325                 330                 335
Pro Lys Gln Lys Val Thr Asp Leu Ile Ser Ile Met Phe Glu Glu Leu
            340                 345                 350
Pro Phe Asn Leu Lys Glu Gln Tyr Glu Ile Tyr Lys Glu Lys Glu Ser
            355                 360                 365
Lys

<210> SEQ ID NO 2
<211> LENGTH: 325
<212> TYPE: PRT
<213> ORGANISM: Geobacillus stearothermophilus

<400> SEQUENCE: 2

Met Ala Gln Met Thr Met Val Gln Ala Ile Thr Asp Ala Leu Arg Ile
1               5                   10                  15
Glu Leu Lys Asn Asp Pro Asn Val Leu Ile Phe Gly Glu Asp Val Gly
            20                  25                  30
Val Asn Gly Gly Val Phe Arg Ala Thr Glu Gly Leu Gln Ala Glu Phe
        35                  40                  45
Gly Glu Asp Arg Val Phe Asp Thr Pro Leu Ala Glu Ser Gly Ile Gly
    50                  55                  60
Gly Leu Ala Ile Gly Leu Ala Leu Gln Gly Phe Arg Pro Val Pro Glu
65                  70                  75                  80
Ile Gln Phe Phe Gly Phe Val Tyr Glu Val Met Asp Ser Ile Cys Gly
                85                  90                  95
Gln Met Ala Arg Ile Arg Tyr Arg Thr Gly Gly Arg Tyr His Met Pro
            100                 105                 110
Ile Thr Ile Arg Ser Pro Phe Gly Gly Gly Val His Thr Pro Glu Leu
```

```
                115                 120                 125
His Ser Asp Ser Leu Glu Gly Leu Val Ala Gln Gln Pro Gly Leu Lys
    130                 135                 140

Val Val Ile Pro Ser Thr Pro Tyr Asp Ala Lys Gly Leu Leu Ile Ser
145                 150                 155                 160

Ala Ile Arg Asp Asn Asp Pro Val Ile Phe Leu Glu His Leu Lys Leu
                165                 170                 175

Tyr Arg Ser Phe Arg Gln Glu Val Pro Glu Gly Glu Tyr Thr Ile Pro
            180                 185                 190

Ile Gly Lys Ala Asp Ile Lys Arg Glu Gly Lys Asp Ile Thr Ile Ile
        195                 200                 205

Ala Tyr Gly Ala Met Val His Glu Ser Leu Lys Ala Ala Ala Glu Leu
    210                 215                 220

Glu Lys Glu Gly Ile Ser Ala Glu Val Val Asp Leu Arg Thr Val Gln
225                 230                 235                 240

Pro Leu Asp Ile Glu Thr Ile Ile Gly Ser Val Glu Lys Thr Gly Arg
                245                 250                 255

Ala Ile Val Val Gln Glu Ala Gln Arg Gln Ala Gly Ile Ala Ala Asn
            260                 265                 270

Val Val Ala Glu Ile Asn Glu Arg Ala Ile Leu Ser Leu Glu Ala Pro
        275                 280                 285

Val Leu Arg Val Ala Ala Pro Asp Thr Val Tyr Pro Phe Ala Gln Ala
    290                 295                 300

Glu Ser Val Trp Leu Pro Asn Phe Lys Asp Val Ile Glu Thr Ala Lys
305                 310                 315                 320

Lys Val Met Asn Phe
                325

<210> SEQ ID NO 3
<211> LENGTH: 428
<212> TYPE: PRT
<213> ORGANISM: Geobacillus stearothermophilus

<400> SEQUENCE: 3

Met Ala Phe Glu Phe Lys Leu Pro Asp Ile Gly Glu Gly Ile His Glu
1               5                   10                  15

Gly Glu Ile Val Lys Trp Phe Val Lys Pro Gly Asp Glu Val Asn Glu
            20                  25                  30

Asp Asp Val Leu Cys Glu Val Gln Asn Asp Lys Ala Val Val Glu Ile
        35                  40                  45

Pro Ser Pro Val Lys Gly Lys Val Leu Glu Ile Leu Val Pro Glu Gly
    50                  55                  60

Thr Val Ala Thr Val Gly Gln Thr Leu Ile Thr Leu Asp Ala Pro Gly
65                  70                  75                  80

Tyr Glu Asn Met Thr Phe Lys Gly Gln Glu Gln Glu Glu Ala Lys Lys
                85                  90                  95

Glu Glu Lys Thr Glu Thr Val Ser Lys Glu Glu Lys Val Asp Ala Val
            100                 105                 110

Ala Pro Asn Ala Pro Ala Ala Glu Ala Glu Ala Gly Pro Asn Arg Arg
        115                 120                 125

Val Ile Ala Met Pro Ser Val Arg Lys Tyr Ala Arg Glu Lys Gly Val
    130                 135                 140

Asp Ile Arg Leu Val Gln Gly Thr Gly Lys Asn Gly Arg Val Leu Lys
145                 150                 155                 160
```

-continued

```
Glu Asp Ile Asp Ala Phe Leu Ala Gly Gly Ala Lys Pro Ala Pro Ala
                165                 170                 175
Ala Ala Glu Glu Lys Ala Ala Pro Ala Ala Lys Pro Ala Thr Thr
        180                 185                 190
Glu Gly Glu Phe Pro Glu Thr Arg Glu Lys Met Ser Gly Ile Arg Arg
        195                 200                 205
Ala Ile Ala Lys Ala Met Val His Ser Lys His Thr Ala Pro His Val
    210                 215                 220
Thr Leu Met Asp Glu Asp Val Thr Lys Leu Val Ala His Arg Lys
225                 230                 235                 240
Lys Phe Lys Ala Ile Ala Ala Glu Lys Gly Ile Lys Leu Thr Phe Leu
                245                 250                 255
Pro Tyr Val Val Lys Ala Leu Val Ser Ala Leu Arg Glu Tyr Pro Val
                260                 265                 270
Leu Asn Thr Ser Ile Asp Asp Glu Thr Glu Glu Ile Ile Gln Lys His
            275                 280                 285
Tyr Tyr Asn Ile Gly Ile Ala Ala Asp Thr Asp Arg Gly Leu Leu Val
        290                 295                 300
Pro Val Ile Lys His Ala Asp Arg Lys Pro Ile Phe Ala Leu Ala Gln
305                 310                 315                 320
Glu Ile Asn Glu Leu Ala Glu Lys Ala Arg Asp Gly Lys Leu Thr Pro
                325                 330                 335
Gly Glu Met Lys Gly Ala Ser Cys Thr Ile Thr Asn Ile Gly Ser Ala
                340                 345                 350
Gly Gly Gln Trp Phe Thr Pro Val Ile Asn His Pro Glu Val Ala Ile
            355                 360                 365
Leu Gly Ile Gly Arg Ile Ala Glu Lys Pro Ile Val Arg Asp Gly Glu
        370                 375                 380
Ile Val Ala Ala Pro Met Leu Ala Leu Ser Leu Ser Phe Asp His Arg
385                 390                 395                 400
Met Ile Asp Gly Ala Thr Ala Gln Lys Ala Leu Asn His Ile Lys Arg
                405                 410                 415
Leu Leu Ser Asp Pro Glu Leu Leu Met Glu Ala
            420                 425

<210> SEQ ID NO 4
<211> LENGTH: 1413
<212> TYPE: DNA
<213> ORGANISM: Geobacillus stearothermophilus
<220> FEATURE:
<221> NAME/KEY: CDS
<222> LOCATION: (1)..(1413)

<400> SEQUENCE: 4 atg gta gtt ggc gat ttt gca att gaa acg gaa acg ctt gtc gtc ggc     48
Met Val Val Gly Asp Phe Ala Ile Glu Thr Glu Thr Leu Val Val Gly
1               5                   10                  15 gcc ggt cct ggc ggg tat gtc gcc gcc atc cgc gcc gcg cag ctc gga     96
Ala Gly Pro Gly Gly Tyr Val Ala Ala Ile Arg Ala Ala Gln Leu Gly
                20                  25                  30 caa aaa gtg acg att gtg gaa aag ggc aat tta ggc ggc gtc tgc tta    144
Gln Lys Val Thr Ile Val Glu Lys Gly Asn Leu Gly Gly Val Cys Leu
            35                  40                  45 aat gtt ggc tgc atc ccg tca aag gcg ctg atc tcc gca agc cat cgc    192
Asn Val Gly Cys Ile Pro Ser Lys Ala Leu Ile Ser Ala Ser His Arg
        50                  55                  60 tat gag cag gcg aag cat tcc gaa gaa atg ggc att aag gcg gag aac    240
```

|   |   |   |   |   |   |   |   |   |   |   |   |   |   |   |   |
|---|---|---|---|---|---|---|---|---|---|---|---|---|---|---|---|
| Tyr | Glu | Gln | Ala | Lys | His | Ser | Glu | Glu | Met | Gly | Ile | Lys | Ala | Glu | Asn |
| 65 |   |   |   | 70 |   |   |   |   | 75 |   |   |   |   | 80 |   |

```
gtc acc atc gat ttt gcc aaa gtg caa gaa tgg aaa gca agc gtc gtg       288
Val Thr Ile Asp Phe Ala Lys Val Gln Glu Trp Lys Ala Ser Val Val
            85                  90                  95 aaa aaa tta acg ggc ggc gtc gaa ggg ctg tta aaa gga aac aaa gta       336
Lys Lys Leu Thr Gly Gly Val Glu Gly Leu Leu Lys Gly Asn Lys Val
            100                 105                 110 gag atc gtc aaa ggg gaa gcg tat ttt gtc gac gcc aat acg gtg cgt       384
Glu Ile Val Lys Gly Glu Ala Tyr Phe Val Asp Ala Asn Thr Val Arg
            115                 120                 125 gtc gtc aac ggc gac agc gcg cag acg tat acg ttc aaa aac gcg att       432
Val Val Asn Gly Asp Ser Ala Gln Thr Tyr Thr Phe Lys Asn Ala Ile
130                 135                 140 atc gcc acc ggc tcg cgc ccg att gag ctg ccg aac ttc aag ttt tcc       480
Ile Ala Thr Gly Ser Arg Pro Ile Glu Leu Pro Asn Phe Lys Phe Ser
145                 150                 155                 160 aac cgc att ctt gac tcg acg gga gct ctc aac ctt ggg gaa gtg ccg       528
Asn Arg Ile Leu Asp Ser Thr Gly Ala Leu Asn Leu Gly Glu Val Pro
                165                 170                 175 aaa tcg ctc gtg gtc atc ggc ggc ggc tat att ggc atc gaa ctc ggt       576
Lys Ser Leu Val Val Ile Gly Gly Gly Tyr Ile Gly Ile Glu Leu Gly
            180                 185                 190 acg gct tac gcc aac ttt ggg acg aaa gtg acc att tta gaa gga gcc       624
Thr Ala Tyr Ala Asn Phe Gly Thr Lys Val Thr Ile Leu Glu Gly Ala
            195                 200                 205 ggc gaa att ttg tcc ggt ttt gag aag caa atg gct gcc atc atc aag       672
Gly Glu Ile Leu Ser Gly Phe Glu Lys Gln Met Ala Ala Ile Ile Lys
210                 215                 220 aag cgc ctg aag aaa aaa ggc gtt gaa gtc gtg acg aac gca ttg gcg       720
Lys Arg Leu Lys Lys Lys Gly Val Glu Val Val Thr Asn Ala Leu Ala
225                 230                 235                 240 aaa ggg gcc gaa gaa cgc gaa gac ggc gtc acg gtc acg tat gag gcg       768
Lys Gly Ala Glu Glu Arg Glu Asp Gly Val Thr Val Thr Tyr Glu Ala
                245                 250                 255 aat ggt gaa acg aaa acg att gac gcc gac tat gtg ctc gtc acc gtc       816
Asn Gly Glu Thr Lys Thr Ile Asp Ala Asp Tyr Val Leu Val Thr Val
            260                 265                 270 ggc cgc cgt ccg aat aca gat gaa ctt ggt ctt gaa caa atc ggc atc       864
Gly Arg Arg Pro Asn Thr Asp Glu Leu Gly Leu Glu Gln Ile Gly Ile
            275                 280                 285 aaa atg acg aac cgc ggc ttg att gaa gtg gac caa caa tgc cgg aca       912
Lys Met Thr Asn Arg Gly Leu Ile Glu Val Asp Gln Gln Cys Arg Thr
290                 295                 300 agc gtg ccg aac att ttt gcg atc ggc gac atc gtt cca ggt ccg gcg       960
Ser Val Pro Asn Ile Phe Ala Ile Gly Asp Ile Val Pro Gly Pro Ala
305                 310                 315                 320 ctc gcc cat aaa gcg tcg tat gaa gga aaa gtg gct gcg gaa gct atc      1008
Leu Ala His Lys Ala Ser Tyr Glu Gly Lys Val Ala Ala Glu Ala Ile
                325                 330                 335 gcc ggc cat ccg tcg gca gtc gat tac gtg gcc att cca gct gtt gtc      1056
Ala Gly His Pro Ser Ala Val Asp Tyr Val Ala Ile Pro Ala Val Val
            340                 345                 350 ttc tcc gat ccg gaa tgc gcg tcg gtc ggc tat ttt gag cag cag gcg      1104
Phe Ser Asp Pro Glu Cys Ala Ser Val Gly Tyr Phe Glu Gln Gln Ala
            355                 360                 365 aaa gac gag ggc att gac gtc att gcc gcg aaa ttc ccg ttt gct gcc      1152
Lys Asp Glu Gly Ile Asp Val Ile Ala Ala Lys Phe Pro Phe Ala Ala
370                 375                 380
```

```
aac ggc cgc gcc ttg gcg ctg aac gat acg gac ggc ttc ttg aag ctc      1200
Asn Gly Arg Ala Leu Ala Leu Asn Asp Thr Asp Gly Phe Leu Lys Leu
385                 390                 395                 400 gtt gtc cgc aaa gag gac ggc gtc atc att ggt gcg caa atc atc ggt      1248
Val Val Arg Lys Glu Asp Gly Val Ile Ile Gly Ala Gln Ile Ile Gly
            405                 410                 415 cca aat gct tct gac atg atc gcc gag ctt ggg ctc gcc att gaa gcc      1296
Pro Asn Ala Ser Asp Met Ile Ala Glu Leu Gly Leu Ala Ile Glu Ala
                420                 425                 430 ggc atg acg gcg gaa gac atc gct ttg acg atc cat gcc cat ccg acg      1344
Gly Met Thr Ala Glu Asp Ile Ala Leu Thr Ile His Ala His Pro Thr
            435                 440                 445 ctt ggc gaa atc gcc atg gaa gcg gcg gaa gtg gcg ctt ggc aca ccg      1392
Leu Gly Glu Ile Ala Met Glu Ala Ala Glu Val Ala Leu Gly Thr Pro
    450                 455                 460 att cat atc att acg aag taa                                          1413
Ile His Ile Ile Thr Lys
465                 470

<210> SEQ ID NO 5
<211> LENGTH: 470
<212> TYPE: PRT
<213> ORGANISM: Geobacillus stearothermophilus

<400> SEQUENCE: 5

Met Val Val Gly Asp Phe Ala Ile Glu Thr Glu Thr Leu Val Val Gly
1               5                   10                  15

Ala Gly Pro Gly Gly Tyr Val Ala Ala Ile Arg Ala Ala Gln Leu Gly
            20                  25                  30

Gln Lys Val Thr Ile Val Glu Lys Gly Asn Leu Gly Gly Val Cys Leu
        35                  40                  45

Asn Val Gly Cys Ile Pro Ser Lys Ala Leu Ile Ser Ala Ser His Arg
    50                  55                  60

Tyr Glu Gln Ala Lys His Ser Glu Glu Met Gly Ile Lys Ala Glu Asn
65                  70                  75                  80

Val Thr Ile Asp Phe Ala Lys Val Gln Glu Trp Lys Ala Ser Val Val
                85                  90                  95

Lys Lys Leu Thr Gly Gly Val Glu Gly Leu Leu Lys Gly Asn Lys Val
            100                 105                 110

Glu Ile Val Lys Gly Glu Ala Tyr Phe Val Asp Ala Asn Thr Val Arg
        115                 120                 125

Val Val Asn Gly Asp Ser Ala Gln Thr Tyr Thr Phe Lys Asn Ala Ile
    130                 135                 140

Ile Ala Thr Gly Ser Arg Pro Ile Glu Leu Pro Asn Phe Lys Phe Ser
145                 150                 155                 160

Asn Arg Ile Leu Asp Ser Thr Gly Ala Leu Asn Leu Gly Glu Val Pro
                165                 170                 175

Lys Ser Leu Val Val Ile Gly Gly Gly Tyr Ile Gly Ile Glu Leu Gly
            180                 185                 190

Thr Ala Tyr Ala Asn Phe Gly Thr Lys Val Thr Ile Leu Glu Gly Ala
        195                 200                 205

Gly Glu Ile Leu Ser Gly Phe Glu Lys Gln Met Ala Ala Ile Ile Lys
    210                 215                 220

Lys Arg Leu Lys Lys Gly Val Glu Val Val Thr Asn Ala Leu Ala
225                 230                 235                 240

Lys Gly Ala Glu Glu Arg Glu Asp Gly Val Thr Val Thr Tyr Glu Ala
                245                 250                 255
```

```
Asn Gly Glu Thr Lys Thr Ile Asp Ala Asp Tyr Val Leu Val Thr Val
            260                 265                 270

Gly Arg Arg Pro Asn Thr Asp Glu Leu Gly Leu Glu Gln Ile Gly Ile
        275                 280                 285

Lys Met Thr Asn Arg Gly Leu Ile Glu Val Asp Gln Gln Cys Arg Thr
    290                 295                 300

Ser Val Pro Asn Ile Phe Ala Ile Gly Asp Ile Val Pro Gly Pro Ala
305                 310                 315                 320

Leu Ala His Lys Ala Ser Tyr Glu Gly Lys Val Ala Ala Glu Ala Ile
                325                 330                 335

Ala Gly His Pro Ser Ala Val Asp Tyr Val Ala Ile Pro Ala Val Val
            340                 345                 350

Phe Ser Asp Pro Glu Cys Ala Ser Val Gly Tyr Phe Glu Gln Gln Ala
        355                 360                 365

Lys Asp Glu Gly Ile Asp Val Ile Ala Ala Lys Phe Pro Phe Ala Ala
    370                 375                 380

Asn Gly Arg Ala Leu Ala Leu Asn Asp Thr Asp Gly Phe Leu Lys Leu
385                 390                 395                 400

Val Val Arg Lys Glu Asp Gly Val Ile Gly Ala Gln Ile Gly
                405                 410                 415

Pro Asn Ala Ser Asp Met Ile Ala Glu Leu Gly Leu Ala Ile Glu Ala
            420                 425                 430

Gly Met Thr Ala Glu Asp Ile Ala Leu Thr Ile His Ala His Pro Thr
        435                 440                 445

Leu Gly Glu Ile Ala Met Glu Ala Ala Glu Val Ala Leu Gly Thr Pro
    450                 455                 460

Ile His Ile Ile Thr Lys
465                 470

<210> SEQ ID NO 6
<211> LENGTH: 1413
<212> TYPE: DNA
<213> ORGANISM: Artificial Sequence
<220> FEATURE:
<223> OTHER INFORMATION: Mutated Dihydrolipoamide dehydrogenase from
      Geobacillus stearothermophilus
<220> FEATURE:
<221> NAME/KEY: CDS
<222> LOCATION: (1)..(1413)

<400> SEQUENCE: 6 atg gta gtt ggc gat ttt gca att gaa acg gaa acg ctt gtc gtc ggc      48
Met Val Val Gly Asp Phe Ala Ile Glu Thr Glu Thr Leu Val Val Gly
1               5                   10                  15 gcc ggt cct ggc ggg tat gtc gcc gcc atc cgc gcc gcg cag ctc gga      96
Ala Gly Pro Gly Gly Tyr Val Ala Ala Ile Arg Ala Ala Gln Leu Gly
                20                  25                  30 caa aaa gtg acg att gtg gaa aag ggc aat tta ggc ggc gtc tgc tta     144
Gln Lys Val Thr Ile Val Glu Lys Gly Asn Leu Gly Gly Val Cys Leu
            35                  40                  45 aat gtt ggc tgc atc ccg tca aag gcg ctg atc tcc gca agc cat cgc     192
Asn Val Gly Cys Ile Pro Ser Lys Ala Leu Ile Ser Ala Ser His Arg
        50                  55                  60 tat gag cag gcg aag cat tcc gaa gaa atg ggc att aag gcg gag aac     240
Tyr Glu Gln Ala Lys His Ser Glu Glu Met Gly Ile Lys Ala Glu Asn
65                  70                  75                  80 gtc acc atc gat ttt gcc aaa gtg caa gaa tgg aaa gca agc gtc gtg     288
Val Thr Ile Asp Phe Ala Lys Val Gln Glu Trp Lys Ala Ser Val Val
```

```
                    85                  90                  95
aaa aaa tta acg ggc ggc gtc gaa ggg ctg tta aaa gga aac aaa gta       336
Lys Lys Leu Thr Gly Gly Val Glu Gly Leu Leu Lys Gly Asn Lys Val
            100                 105                 110 gag atc gtc aaa ggg gaa gcg tat ttt gtc gac gcc aat acg gtg cgt       384
Glu Ile Val Lys Gly Glu Ala Tyr Phe Val Asp Ala Asn Thr Val Arg
            115                 120                 125 gtc gtc aac ggc gac agc gcg cag acg tat acg ttc aaa aac gcg att       432
Val Val Asn Gly Asp Ser Ala Gln Thr Tyr Thr Phe Lys Asn Ala Ile
130                 135                 140 atc gcc acc ggc tcg cgc ccg att gag ctg ccg aac ttc aag ttt tcc       480
Ile Ala Thr Gly Ser Arg Pro Ile Glu Leu Pro Asn Phe Lys Phe Ser
145                 150                 155                 160 aac cgc att ctt gac tcg acg gga gct ctc aac ctt ggg gaa gtg ccg       528
Asn Arg Ile Leu Asp Ser Thr Gly Ala Leu Asn Leu Gly Glu Val Pro
                165                 170                 175 aaa tcg ctc gtg gtc atc ggc ggc tat att gcg atc gaa ctc gcg           576
Lys Ser Leu Val Val Ile Gly Gly Tyr Ile Ala Ile Glu Leu Ala
            180                 185                 190 acg gct tac gcc aac ttt ggg acg aaa gtg acc att tta gtg cgt aaa       624
Thr Ala Tyr Ala Asn Phe Gly Thr Lys Val Thr Ile Leu Val Arg Lys
            195                 200                 205 ggc gaa att ttg cgt ggt ttt gag aag caa atg gct gcc atc atc aag       672
Gly Glu Ile Leu Arg Gly Phe Glu Lys Gln Met Ala Ala Ile Ile Lys
210                 215                 220 aag cgc ctg aag aaa aaa ggc gtt gaa gtc gtg acg aac gca ttg gcg       720
Lys Arg Leu Lys Lys Lys Gly Val Glu Val Val Thr Asn Ala Leu Ala
225                 230                 235                 240 aaa ggg gcc gaa gaa cgc gaa gac ggc gtc acg gtc acg tat gag gcg       768
Lys Gly Ala Glu Glu Arg Glu Asp Gly Val Thr Val Thr Tyr Glu Ala
                245                 250                 255 aat ggt gaa acg aaa acg att gac gcc gac tat gtg ctc gtc acc gtc       816
Asn Gly Glu Thr Lys Thr Ile Asp Ala Asp Tyr Val Leu Val Thr Val
            260                 265                 270 ggc cgc cgt ccg aat aca gat gaa ctt ggt ctt gaa caa atc ggc atc       864
Gly Arg Arg Pro Asn Thr Asp Glu Leu Gly Leu Glu Gln Ile Gly Ile
            275                 280                 285 aaa atg acg aac cgc ggc ttg att gaa gtg gac caa caa tgc cgg aca       912
Lys Met Thr Asn Arg Gly Leu Ile Glu Val Asp Gln Gln Cys Arg Thr
290                 295                 300 agc gtg ccg aac att ttt gcg atc ggc gac atc gtt cca ggt ccg gcg       960
Ser Val Pro Asn Ile Phe Ala Ile Gly Asp Ile Val Pro Gly Pro Ala
305                 310                 315                 320 ctc gcc cat aaa gcg tcg tat gaa gga aaa gtg gct gcg gaa gct atc       1008
Leu Ala His Lys Ala Ser Tyr Glu Gly Lys Val Ala Ala Glu Ala Ile
                325                 330                 335 gcc ggc cat ccg tcg gca gtc gat tac gtg gcc att cca gct gtt gtc       1056
Ala Gly His Pro Ser Ala Val Asp Tyr Val Ala Ile Pro Ala Val Val
            340                 345                 350 ttc tcc gat ccg gaa tgc gcg tcg gtc ggc tat ttt gag cag cag gcg       1104
Phe Ser Asp Pro Glu Cys Ala Ser Val Gly Tyr Phe Glu Gln Gln Ala
            355                 360                 365 aaa gac gag ggc att gac gtc att gcc gcg aaa ttc ccg ttt gct gcc       1152
Lys Asp Glu Gly Ile Asp Val Ile Ala Ala Lys Phe Pro Phe Ala Ala
370                 375                 380 aac ggc cgc gcc ttg gcg ctg aac gat acg gac ggc ttc ttg aag ctc       1200
Asn Gly Arg Ala Leu Ala Leu Asn Asp Thr Asp Gly Phe Leu Lys Leu
385                 390                 395                 400 gtt gtc cgc aaa gag gac ggc gtc atc att ggt gcg caa atc atc ggt       1248
Val Val Arg Lys Glu Asp Gly Val Ile Ile Gly Ala Gln Ile Ile Gly
```

```
Val Val Arg Lys Glu Asp Gly Val Ile Ile Gly Ala Gln Ile Ile Gly
                405                 410                 415 cca aat gct tct gac atg atc gcc gag ctt ggg ctc gcc att gaa gcc      1296
Pro Asn Ala Ser Asp Met Ile Ala Glu Leu Gly Leu Ala Ile Glu Ala
            420                 425                 430 ggc atg acg gcg gaa gac atc gct ttg acg atc cat gcc cat ccg acg      1344
Gly Met Thr Ala Glu Asp Ile Ala Leu Thr Ile His Ala His Pro Thr
        435                 440                 445 ctt ggc gaa atc gcc atg gaa gcg gcg gaa gtg gcg ctt ggc aca ccg      1392
Leu Gly Glu Ile Ala Met Glu Ala Ala Glu Val Ala Leu Gly Thr Pro
    450                 455                 460 att cat atc att acg aag taa                                          1413
Ile His Ile Ile Thr Lys
465                 470

<210> SEQ ID NO 7
<211> LENGTH: 470
<212> TYPE: PRT
<213> ORGANISM: Artificial Sequence
<220> FEATURE:
<223> OTHER INFORMATION: Synthetic Construct

<400> SEQUENCE: 7

Met Val Val Gly Asp Phe Ala Ile Glu Thr Glu Thr Leu Val Val Gly
1               5                   10                  15

Ala Gly Pro Gly Gly Tyr Val Ala Ala Ile Arg Ala Ala Gln Leu Gly
            20                  25                  30

Gln Lys Val Thr Ile Val Glu Lys Gly Asn Leu Gly Gly Val Cys Leu
        35                  40                  45

Asn Val Gly Cys Ile Pro Ser Lys Ala Leu Ile Ser Ala Ser His Arg
    50                  55                  60

Tyr Glu Gln Ala Lys His Ser Glu Glu Met Gly Ile Lys Ala Glu Asn
65                  70                  75                  80

Val Thr Ile Asp Phe Ala Lys Val Gln Glu Trp Lys Ala Ser Val Val
                85                  90                  95

Lys Lys Leu Thr Gly Gly Val Glu Gly Leu Leu Lys Gly Asn Lys Val
            100                 105                 110

Glu Ile Val Lys Gly Glu Ala Tyr Phe Val Asp Ala Asn Thr Val Arg
        115                 120                 125

Val Val Asn Gly Asp Ser Ala Gln Thr Tyr Thr Phe Lys Asn Ala Ile
    130                 135                 140

Ile Ala Thr Gly Ser Arg Pro Ile Glu Leu Pro Asn Phe Lys Phe Ser
145                 150                 155                 160

Asn Arg Ile Leu Asp Ser Thr Gly Ala Leu Asn Leu Gly Glu Val Pro
                165                 170                 175

Lys Ser Leu Val Val Ile Gly Gly Tyr Ile Ala Ile Glu Leu Ala
            180                 185                 190

Thr Ala Tyr Ala Asn Phe Gly Thr Lys Val Thr Ile Leu Val Arg Lys
        195                 200                 205

Gly Glu Ile Leu Arg Gly Phe Glu Lys Gln Met Ala Ala Ile Ile Lys
    210                 215                 220

Lys Arg Leu Lys Lys Gly Val Glu Val Thr Asn Ala Leu Ala
225                 230                 235                 240

Lys Gly Ala Glu Glu Arg Glu Asp Gly Val Thr Val Thr Tyr Glu Ala
                245                 250                 255

Asn Gly Glu Thr Lys Thr Ile Asp Ala Asp Tyr Val Leu Val Thr Val
            260                 265                 270
```

```
Gly Arg Arg Pro Asn Thr Asp Glu Leu Gly Leu Glu Gln Ile Gly Ile
            275                 280                 285

Lys Met Thr Asn Arg Gly Leu Ile Glu Val Asp Gln Gln Cys Arg Thr
            290                 295                 300

Ser Val Pro Asn Ile Phe Ala Ile Gly Asp Ile Val Pro Gly Pro Ala
305                 310                 315                 320

Leu Ala His Lys Ala Ser Tyr Glu Gly Lys Val Ala Ala Glu Ala Ile
            325                 330                 335

Ala Gly His Pro Ser Ala Val Asp Tyr Val Ala Ile Pro Ala Val Val
            340                 345                 350

Phe Ser Asp Pro Glu Cys Ala Ser Val Gly Tyr Phe Glu Gln Gln Ala
            355                 360                 365

Lys Asp Glu Gly Ile Asp Val Ile Ala Ala Lys Phe Pro Phe Ala Ala
            370                 375                 380

Asn Gly Arg Ala Leu Ala Leu Asn Asp Thr Asp Gly Phe Leu Lys Leu
385                 390                 395                 400

Val Val Arg Lys Glu Asp Gly Val Ile Ile Gly Ala Gln Ile Ile Gly
            405                 410                 415

Pro Asn Ala Ser Asp Met Ile Ala Glu Leu Gly Leu Ala Ile Glu Ala
            420                 425                 430

Gly Met Thr Ala Glu Asp Ile Ala Leu Thr Ile His Ala His Pro Thr
            435                 440                 445

Leu Gly Glu Ile Ala Met Glu Ala Ala Glu Val Ala Leu Gly Thr Pro
            450                 455                 460

Ile His Ile Ile Thr Lys
465                 470

<210> SEQ ID NO 8
<211> LENGTH: 338
<212> TYPE: PRT
<213> ORGANISM: Escherichia coli

<400> SEQUENCE: 8

Met Ser Thr Leu Arg Leu Leu Ile Ser Asp Ser Tyr Asp Pro Trp Phe
1               5                   10                  15

Asn Leu Ala Val Glu Glu Cys Ile Phe Arg Gln Met Pro Ala Thr Gln
            20                  25                  30

Arg Val Leu Phe Leu Trp Arg Asn Ala Asp Thr Val Val Ile Gly Arg
            35                  40                  45

Ala Gln Asn Pro Trp Lys Glu Cys Asn Thr Arg Arg Met Glu Glu Asp
            50                  55                  60

Asn Val Arg Leu Ala Arg Arg Ser Ser Gly Gly Gly Ala Val Phe His
65                  70                  75                  80

Asp Leu Gly Asn Thr Cys Phe Thr Phe Met Ala Gly Lys Pro Glu Tyr
            85                  90                  95

Asp Lys Thr Ile Ser Thr Ser Ile Val Leu Asn Ala Leu Asn Ala Leu
            100                 105                 110

Gly Val Ser Ala Glu Ala Ser Gly Arg Asn Asp Leu Val Val Lys Thr
            115                 120                 125

Val Glu Gly Asp Arg Lys Val Ser Gly Ser Ala Tyr Arg Glu Thr Lys
            130                 135                 140

Asp Arg Gly Phe His His Gly Thr Leu Leu Leu Asn Ala Asp Leu Ser
145                 150                 155                 160

Arg Leu Ala Asn Tyr Leu Asn Pro Asp Lys Lys Lys Leu Ala Ala Lys
```

```
            165                 170                 175
Gly Ile Thr Ser Val Arg Ser Arg Val Thr Asn Leu Thr Glu Leu Leu
            180                 185                 190

Pro Gly Ile Thr His Glu Gln Val Cys Glu Ala Ile Thr Glu Ala Phe
            195                 200                 205

Phe Ala His Tyr Gly Glu Arg Val Glu Ala Glu Ile Ile Ser Pro Asn
            210                 215                 220

Lys Thr Pro Asp Leu Pro Asn Phe Ala Glu Thr Phe Ala Arg Gln Ser
225                 230                 235                 240

Ser Trp Glu Trp Asn Phe Gly Gln Ala Pro Ala Phe Ser His Leu Leu
                245                 250                 255

Asp Glu Arg Phe Thr Trp Gly Gly Val Glu Leu His Phe Asp Val Glu
                260                 265                 270

Lys Gly His Ile Thr Arg Ala Gln Val Phe Thr Asp Ser Leu Asn Pro
            275                 280                 285

Ala Pro Leu Glu Ala Leu Ala Gly Arg Leu Gln Gly Cys Leu Tyr Arg
290                 295                 300

Ala Asp Met Leu Gln Gln Glu Cys Glu Ala Leu Leu Val Asp Phe Pro
305                 310                 315                 320

Glu Gln Glu Lys Glu Leu Arg Glu Leu Ser Ala Trp Met Ala Gly Ala
                325                 330                 335

Val Arg

<210> SEQ ID NO 9
<211> LENGTH: 1341
<212> TYPE: DNA
<213> ORGANISM: Lactococcus lactis
<220> FEATURE:
<221> NAME/KEY: CDS
<222> LOCATION: (1)..(1341)

<400> SEQUENCE: 9 atg aaa atc gta gtt atc ggt acg aac cac gca ggc att gct aca gca      48
Met Lys Ile Val Val Ile Gly Thr Asn His Ala Gly Ile Ala Thr Ala
1               5                  10                  15 aat aca tta att gat cga tat cca ggc cat gag att gtt atg att gac      96
Asn Thr Leu Ile Asp Arg Tyr Pro Gly His Glu Ile Val Met Ile Asp
            20                  25                  30 cgt aac agt aat atg agt tac ttg ggg tgt ggg aca gct att tgg gtc     144
Arg Asn Ser Asn Met Ser Tyr Leu Gly Cys Gly Thr Ala Ile Trp Val
        35                  40                  45 gga aga caa att gaa aaa cca gat gag ctg ttt tat gcc aaa gca gaa     192
Gly Arg Gln Ile Glu Lys Pro Asp Glu Leu Phe Tyr Ala Lys Ala Glu
    50                  55                  60 gat ttt gaa aaa aag gga gta aag ata tta aca gaa aca gaa gtt tca     240
Asp Phe Glu Lys Lys Gly Val Lys Ile Leu Thr Glu Thr Glu Val Ser
65                  70                  75                  80 gaa att gac ttt act aat aaa atg att tat gcc aag tca aaa act gga     288
Glu Ile Asp Phe Thr Asn Lys Met Ile Tyr Ala Lys Ser Lys Thr Gly
                85                  90                  95 gaa aag att aca gaa agt tat gat aaa ctc gtt ctg gca aca ggt tca     336
Glu Lys Ile Thr Glu Ser Tyr Asp Lys Leu Val Leu Ala Thr Gly Ser
            100                 105                 110 cgt cca att att cct aac ttg cca gga aaa gat ctt aaa ggc att cat     384
Arg Pro Ile Ile Pro Asn Leu Pro Gly Lys Asp Leu Lys Gly Ile His
        115                 120                 125 ttt tta aaa ctt ttt caa gaa ggg caa gcc att gac gaa gag ttt gct     432
Phe Leu Lys Leu Phe Gln Glu Gly Gln Ala Ile Asp Glu Glu Phe Ala
```

|  |  |  |  |  |  |  |  |  |  |  |  |  |  |  |  |
|---|---|---|---|---|---|---|---|---|---|---|---|---|---|---|---|
|  |  | 130 |  |  |  | 135 |  |  |  |  | 140 |  |  |  |  |
| aag | aat | gat | gtg | aaa | cgg | att | gct | gtg | att | ggt | gct | ggt | tat | att | ggg | 480 |
| Lys | Asn | Asp | Val | Lys | Arg | Ile | Ala | Val | Ile | Gly | Ala | Gly | Tyr | Ile | Gly |
| 145 |  |  |  | 150 |  |  |  |  | 155 |  |  |  |  | 160 |

| aca | gaa | att | gct | gaa | gct | gcc | aaa | cgt | cgt | gga | aaa | gaa | gtc | cta | ctt | 528 |
| Thr | Glu | Ile | Ala | Glu | Ala | Ala | Lys | Arg | Arg | Gly | Lys | Glu | Val | Leu | Leu |
|  |  |  |  | 165 |  |  |  |  | 170 |  |  |  |  | 175 |

| ttt | gat | gca | gaa | agt | act | tca | ctt | gct | tca | tat | tat | gat | gaa | gag | ttt | 576 |
| Phe | Asp | Ala | Glu | Ser | Thr | Ser | Leu | Ala | Ser | Tyr | Tyr | Asp | Glu | Glu | Phe |
|  |  |  |  | 180 |  |  |  |  | 185 |  |  |  |  | 190 |

| gct | aaa | ggg | atg | gat | gaa | aat | ctt | gcc | caa | cat | gga | att | gaa | ctc | cat | 624 |
| Ala | Lys | Gly | Met | Asp | Glu | Asn | Leu | Ala | Gln | His | Gly | Ile | Glu | Leu | His |
|  |  |  |  | 195 |  |  |  |  | 200 |  |  |  |  | 205 |

| ttt | ggg | gaa | tta | gct | caa | gag | ttt | aag | gca | aat | gaa | aaa | ggt | cat | gta | 672 |
| Phe | Gly | Glu | Leu | Ala | Gln | Glu | Phe | Lys | Ala | Asn | Glu | Lys | Gly | His | Val |
|  |  | 210 |  |  |  |  | 215 |  |  |  |  | 220 |

| tca | cag | att | gta | act | aat | aaa | tca | act | tat | gat | gtt | gac | ctc | gtt | att | 720 |
| Ser | Gln | Ile | Val | Thr | Asn | Lys | Ser | Thr | Tyr | Asp | Val | Asp | Leu | Val | Ile |
| 225 |  |  |  | 230 |  |  |  |  | 235 |  |  |  |  | 240 |

| aat | tgt | att | ggc | ttt | aca | gcc | aat | agt | gca | ttg | gct | ggt | gaa | cat | tta | 768 |
| Asn | Cys | Ile | Gly | Phe | Thr | Ala | Asn | Ser | Ala | Leu | Ala | Gly | Glu | His | Leu |
|  |  |  |  | 245 |  |  |  |  | 250 |  |  |  |  | 255 |

| gaa | acc | ttt | aaa | aat | gga | gca | atc | aaa | gtg | gat | aaa | cat | caa | caa | agt | 816 |
| Glu | Thr | Phe | Lys | Asn | Gly | Ala | Ile | Lys | Val | Asp | Lys | His | Gln | Gln | Ser |
|  |  |  |  | 260 |  |  |  |  | 265 |  |  |  |  | 270 |

| agt | gac | cca | gat | gtt | tct | gct | gta | gga | gat | gtt | gcc | aca | atc | tat | tct | 864 |
| Ser | Asp | Pro | Asp | Val | Ser | Ala | Val | Gly | Asp | Val | Ala | Thr | Ile | Tyr | Ser |
|  |  | 275 |  |  |  |  | 280 |  |  |  |  | 285 |

| aat | gct | tta | caa | gac | ttc | acc | tac | att | gcc | ctt | gcc | tca | aac | gct | gtt | 912 |
| Asn | Ala | Leu | Gln | Asp | Phe | Thr | Tyr | Ile | Ala | Leu | Ala | Ser | Asn | Ala | Val |
|  |  | 290 |  |  |  |  | 295 |  |  |  |  | 300 |

| cgc | tca | ggg | att | gtt | gct | ggt | cat | aat | att | gga | gga | aaa | tca | ata | gag | 960 |
| Arg | Ser | Gly | Ile | Val | Ala | Gly | His | Asn | Ile | Gly | Gly | Lys | Ser | Ile | Glu |
| 305 |  |  |  | 310 |  |  |  |  | 315 |  |  |  |  | 320 |

| tct | gtt | ggt | gta | caa | ggt | tct | aat | gga | atc | tct | att | ttt | ggt | tac | aat | 1008 |
| Ser | Val | Gly | Val | Gln | Gly | Ser | Asn | Gly | Ile | Ser | Ile | Phe | Gly | Tyr | Asn |
|  |  |  |  | 325 |  |  |  |  | 330 |  |  |  |  | 335 |

| atg | act | tct | acg | ggc | ttg | tcg | gtt | aaa | gct | gcg | aaa | aaa | atc | ggc | cta | 1056 |
| Met | Thr | Ser | Thr | Gly | Leu | Ser | Val | Lys | Ala | Ala | Lys | Lys | Ile | Gly | Leu |
|  |  |  |  | 340 |  |  |  |  | 345 |  |  |  |  | 350 |

| gaa | gtt | tca | ttt | agt | gat | ttt | gaa | gat | aag | caa | aaa | gca | tgg | ttc | ctt | 1104 |
| Glu | Val | Ser | Phe | Ser | Asp | Phe | Glu | Asp | Lys | Gln | Lys | Ala | Trp | Phe | Leu |
|  |  | 355 |  |  |  |  | 360 |  |  |  |  | 365 |

| cat | gaa | aat | aat | gat | agt | gtg | aaa | att | cgt | atc | gtt | tat | gaa | aca | aaa | 1152 |
| His | Glu | Asn | Asn | Asp | Ser | Val | Lys | Ile | Arg | Ile | Val | Tyr | Glu | Thr | Lys |
|  |  | 370 |  |  |  |  | 375 |  |  |  |  | 380 |

| aat | cgc | aga | att | att | ggt | gct | caa | ctt | gct | agc | aag | agt | gaa | ata | att | 1200 |
| Asn | Arg | Arg | Ile | Ile | Gly | Ala | Gln | Leu | Ala | Ser | Lys | Ser | Glu | Ile | Ile |
| 385 |  |  |  | 390 |  |  |  |  | 395 |  |  |  |  | 400 |

| gca | gga | aat | att | aat | atg | ttt | agt | tta | gct | att | caa | gaa | aag | aaa | acg | 1248 |
| Ala | Gly | Asn | Ile | Asn | Met | Phe | Ser | Leu | Ala | Ile | Gln | Glu | Lys | Lys | Thr |
|  |  |  |  | 405 |  |  |  |  | 410 |  |  |  |  | 415 |

| att | gat | gaa | tta | gcc | tta | ctt | gat | tta | ttc | ttc | tta | cca | cac | ttc | aat | 1296 |
| Ile | Asp | Glu | Leu | Ala | Leu | Leu | Asp | Leu | Phe | Phe | Leu | Pro | His | Phe | Asn |
|  |  |  |  | 420 |  |  |  |  | 425 |  |  |  |  | 430 |

| agt | cca | tat | aat | tac | atg | act | gtt | gca | gct | tta | aat | gca | aaa | taa |  | 1341 |
| Ser | Pro | Tyr | Asn | Tyr | Met | Thr | Val | Ala | Ala | Leu | Asn | Ala | Lys |
|  |  | 435 |  |  |  |  | 440 |  |  |  |  | 445 |

```
<210> SEQ ID NO 10
<211> LENGTH: 446
<212> TYPE: PRT
<213> ORGANISM: Lactococcus lactis

<400> SEQUENCE: 10

Met Lys Ile Val Val Ile Gly Thr Asn His Ala Gly Ile Ala Thr Ala
1               5                   10                  15

Asn Thr Leu Ile Asp Arg Tyr Pro Gly His Glu Ile Val Met Ile Asp
                20                  25                  30

Arg Asn Ser Asn Met Ser Tyr Leu Gly Cys Gly Thr Ala Ile Trp Val
            35                  40                  45

Gly Arg Gln Ile Glu Lys Pro Asp Glu Leu Phe Tyr Ala Lys Ala Glu
        50                  55                  60

Asp Phe Glu Lys Lys Gly Val Lys Ile Leu Thr Glu Thr Glu Val Ser
65                  70                  75                  80

Glu Ile Asp Phe Thr Asn Lys Met Ile Tyr Ala Lys Ser Lys Thr Gly
                85                  90                  95

Glu Lys Ile Thr Glu Ser Tyr Asp Lys Leu Val Leu Ala Thr Gly Ser
            100                 105                 110

Arg Pro Ile Ile Pro Asn Leu Pro Gly Lys Leu Lys Gly Ile His
        115                 120                 125

Phe Leu Lys Leu Phe Gln Glu Gly Gln Ala Ile Asp Glu Glu Phe Ala
130                 135                 140

Lys Asn Asp Val Lys Arg Ile Ala Val Ile Gly Ala Gly Tyr Ile Gly
145                 150                 155                 160

Thr Glu Ile Ala Glu Ala Ala Lys Arg Arg Gly Lys Glu Val Leu Leu
                165                 170                 175

Phe Asp Ala Glu Ser Thr Ser Leu Ala Ser Tyr Tyr Asp Glu Glu Phe
            180                 185                 190

Ala Lys Gly Met Asp Glu Asn Leu Ala Gln His Gly Ile Glu Leu His
        195                 200                 205

Phe Gly Glu Leu Ala Gln Glu Phe Lys Ala Asn Glu Lys Gly His Val
210                 215                 220

Ser Gln Ile Val Thr Asn Lys Ser Thr Tyr Asp Val Asp Leu Val Ile
225                 230                 235                 240

Asn Cys Ile Gly Phe Thr Ala Asn Ser Ala Leu Ala Gly Glu His Leu
                245                 250                 255

Glu Thr Phe Lys Asn Gly Ala Ile Lys Val Asp Lys His Gln Gln Ser
            260                 265                 270

Ser Asp Pro Asp Val Ser Ala Val Gly Asp Val Ala Thr Ile Tyr Ser
        275                 280                 285

Asn Ala Leu Gln Asp Phe Thr Tyr Ile Ala Leu Ala Ser Asn Ala Val
290                 295                 300

Arg Ser Gly Ile Val Ala Gly His Asn Ile Gly Gly Lys Ser Ile Glu
305                 310                 315                 320

Ser Val Gly Val Gln Gly Ser Asn Gly Ile Ser Ile Phe Gly Tyr Asn
                325                 330                 335

Met Thr Ser Thr Gly Leu Ser Val Lys Ala Ala Lys Ile Gly Leu
            340                 345                 350

Glu Val Ser Phe Ser Asp Phe Glu Asp Lys Gln Lys Ala Trp Phe Leu
        355                 360                 365

His Glu Asn Asn Asp Ser Val Lys Ile Arg Ile Val Tyr Glu Thr Lys
370                 375                 380
```

Asn Arg Arg Ile Ile Gly Ala Gln Leu Ala Ser Lys Ser Glu Ile Ile
385                 390                 395                 400

Ala Gly Asn Ile Asn Met Phe Ser Leu Ala Ile Gln Glu Lys Lys Thr
            405                 410                 415

Ile Asp Glu Leu Ala Leu Leu Asp Leu Phe Phe Leu Pro His Phe Asn
        420                 425                 430

Ser Pro Tyr Asn Tyr Met Thr Val Ala Ala Leu Asn Ala Lys
    435                 440                 445

<210> SEQ ID NO 11
<211> LENGTH: 393
<212> TYPE: PRT
<213> ORGANISM: Ralstonia eutropha

<400> SEQUENCE: 11

Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
        195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
            325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
            355                 360                 365

Arg Asp Ala Lys Lys Gly Leu Ala Ser Leu Cys Ile Gly Gly Gly Met
        370                 375                 380

Gly Val Ala Leu Ala Val Glu Arg Lys
385                 390

<210> SEQ ID NO 12
<211> LENGTH: 246
<212> TYPE: PRT
<213> ORGANISM: Ralstonia eutropha

<400> SEQUENCE: 12

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 13
<211> LENGTH: 605
<212> TYPE: PRT
<213> ORGANISM: Cupriavidus necator

<400> SEQUENCE: 13

```
Met Ala Thr Gly Lys Gly Ala Ala Ser Gly Gln Glu Lys Thr
1               5                   10                  15

Thr Pro Phe Ser Ser Thr Pro Gly Pro Phe Asp Pro Ala Thr Trp Leu
                20                  25                  30

Glu Trp Ser Arg Gln Ala Gln Ala Asn Gly Arg Ala Ala Gly Gly Met
            35                  40                  45

Pro Gly Ala Asp Ala Phe Ala Ala Leu Gly Ala Phe Pro Gly Gly Ala
    50                  55                  60

Phe Pro Gly Ala Gly Phe Pro Gly Thr Ala Phe Pro Gly Ile Lys Ile
65                  70                  75                  80

Ala Pro Ala Gln Leu Ala Glu Ile Gln Gln Arg Phe Met Gln Gly Phe
                85                  90                  95

Thr Asp Leu Trp Arg Ala Met Ala Ala Gly Asp Gln Gln Val Gln
                100                 105                 110

Leu Thr Asp Arg Arg Phe Ala Gly Asp Ala Trp Arg Ser Asn Ala Pro
            115                 120                 125

Tyr Arg Tyr Ala Ala Ala Phe Tyr Leu Leu Thr Ala Arg Ala Met Ser
    130                 135                 140

Glu Met Ala Asp Ala Val Glu Ala Asp Ala Lys Thr Arg Gln Arg Ile
145                 150                 155                 160

Arg Phe Ala Val Thr Gln Trp Val Asp Ala Met Ser Pro Ala Asn Phe
                165                 170                 175

Leu Ala Thr Asn Pro Glu Ala Gln Arg Arg Leu Ile Glu Ser Asn Gly
            180                 185                 190

Glu Ser Leu Arg Ala Gly Leu Arg Asn Met Leu Glu Asp Leu Thr Arg
    195                 200                 205

Gly Lys Ile Ser Gln Thr Asp Glu Ser Ala Phe Glu Val Gly Arg Asn
210                 215                 220

Val Ala Val Thr Glu Gly Ala Val Val Tyr Glu Asn Glu Tyr Phe Gln
225                 230                 235                 240

Leu Leu Gln Tyr Lys Pro Leu Thr Ala Lys Val His Ala Arg Pro Leu
                245                 250                 255

Leu Met Val Pro Pro Cys Ile Asn Lys Tyr Tyr Ile Leu Asp Leu Gln
                260                 265                 270

Pro Glu Ser Ser Leu Val Arg His Ile Val Glu Gln Gly His Thr Val
    275                 280                 285

Phe Leu Val Ser Trp Arg Asn Pro Asp Ala Ser Met Ala Ala Arg Thr
    290                 295                 300

Trp Asp Asp Tyr Ile Glu His Gly Ala Ile Ala Ile Glu Val Ala
305                 310                 315                 320

Arg Ala Ile Ser Gly Gln Pro Arg Ile Asn Val Leu Gly Phe Cys Val
                325                 330                 335

Gly Gly Thr Ile Val Ser Thr Ala Leu Ala Val Met Ala Gly Arg Gly
            340                 345                 350

Glu Arg Pro Ala Gln Ser Leu Thr Leu Thr Thr Leu Leu Asp Phe
    355                 360                 365

Ser Asp Thr Gly Val Leu Asp Val Phe Val Asp Glu Ala His Val Gln
    370                 375                 380

Leu Arg Glu Ala Thr Leu Gly Gly Ala Ala Gly Ala Pro Cys Ala Leu
385                 390                 395                 400

Leu Arg Gly Ile Glu Leu Ala Asn Thr Phe Ser Phe Leu Arg Pro Asn
                405                 410                 415
```

```
Asp Leu Val Trp Asn Tyr Val Val Asp Asn Tyr Leu Lys Gly Asn Thr
            420                 425                 430

Pro Val Pro Phe Asp Leu Leu Phe Trp Asn Gly Asp Ala Thr Asn Leu
        435                 440                 445

Pro Gly Pro Trp Tyr Cys Trp Tyr Leu Arg His Thr Tyr Leu Gln Asp
    450                 455                 460

Glu Leu Lys Val Pro Gly Lys Leu Thr Val Cys Gly Val Pro Val Asp
465                 470                 475                 480

Leu Gly Lys Ile Asp Val Pro Thr Tyr Leu Tyr Gly Ser Arg Glu Asp
                485                 490                 495

His Ile Val Pro Trp Thr Ala Ala Tyr Ala Ser Thr Arg Leu Leu Ser
            500                 505                 510

Asn Asp Leu Arg Phe Val Leu Gly Ala Ser Gly His Ile Ala Gly Val
        515                 520                 525

Ile Asn Pro Pro Ala Lys Asn Lys Arg Ser His Trp Leu Asn Glu Asp
    530                 535                 540

Leu Pro Asp Ser Pro Asn Asp Trp Leu Ala Gly Ala Thr Glu Ala Pro
545                 550                 555                 560

Gly Ser Trp Trp Pro Asp Trp Phe Ala Trp Leu Gly Lys His Ala Gly
                565                 570                 575

Ala Lys Lys Ala Ala Pro Thr Gln Tyr Gly Ser Arg Asp Tyr Pro Ala
            580                 585                 590

Ile Glu Pro Ala Pro Gly Arg Tyr Val Lys Ala Lys Ala
        595                 600                 605

<210> SEQ ID NO 14
<211> LENGTH: 803
<212> TYPE: PRT
<213> ORGANISM: Enterococcus faecalis

<400> SEQUENCE: 14

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
            180                 185                 190
```

```
Phe Ala Asp Glu Ile Ala Pro Leu Glu Val Ser Gly Thr Leu Val Glu
            195                 200                 205

Lys Asp Glu Gly Ile Arg Pro Asn Ser Ser Val Glu Lys Leu Gly Thr
210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
            245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
            275                 280                 285

Ala Ile Gln Lys Leu Leu Ala Arg Asn Gln Leu Thr Thr Glu Glu Ile
            290                 295                 300

Asp Leu Tyr Glu Ile Asn Glu Ala Phe Ala Ala Thr Ser Ile Val Val
305                 310                 315                 320

Gln Arg Glu Leu Ala Leu Pro Glu Glu Lys Val Asn Ile Tyr Gly Gly
            325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Lys Tyr Gly Val
            355                 360                 365

Ala Ser Leu Cys Ile Gly Gly Gly Leu Gly Leu Ala Met Leu Leu Glu
            370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
            405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Glu Val Pro Met Gly Val Gly
            435                 440                 445

Leu His Leu Thr Val Asp Glu Thr Asp Tyr Leu Val Pro Met Ala Thr
            450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
            485                 490                 495

Val Phe Tyr Asp Val Ala Asp Ala Glu Ser Leu Ile Asp Glu Leu Gln
            500                 505                 510

Val Arg Glu Thr Glu Ile Phe Gln Gln Ala Glu Leu Ser Tyr Pro Ser
            515                 520                 525

Ile Val Lys Arg Gly Gly Gly Leu Arg Asp Leu Gln Tyr Arg Ala Phe
            530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
            565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
            595                 600                 605
```

-continued

```
Ser Arg Leu Ser Lys Gly Ser Asn Gly Arg Glu Ile Ala Glu Lys Ile
    610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
                660                 665                 670

Lys Glu Gly Arg Tyr Gln Gly Leu Thr Ser Trp Thr Leu Asp Gly Glu
                675                 680                 685

Gln Leu Ile Gly Glu Ile Ser Val Pro Leu Ala Leu Ala Thr Val Gly
    690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
                740                 745                 750

Gln Lys Gly His Met Ala Leu Gln Ala Arg Ser Leu Ala Met Thr Val
                755                 760                 765

Gly Ala Thr Gly Lys Glu Val Glu Ala Val Ala Gln Gln Leu Lys Arg
    770                 775                 780

Gln Lys Thr Met Asn Gln Asp Arg Ala Leu Ala Ile Leu Asn Asp Leu
785                 790                 795                 800

Arg Lys Gln
```

<210> SEQ ID NO 15
<211> LENGTH: 383
<212> TYPE: PRT
<213> ORGANISM: Artificial Sequence
<220> FEATURE:
<223> OTHER INFORMATION: Mutant Hydroxymethylglutaryl-CoA synthase
      from Enterococcus faecalis

<400> SEQUENCE: 15

```
Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
                20                  25                  30

Phe His Ile Gly Ile Gly Gln Asp Gln Met Ala Val Asn Pro Ile Ser
            35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Gly Cys Tyr
                100                 105                 110

Gly Ala Thr Ala Gly Leu Gln Leu Ala Lys Asn His Val Ala Leu His
            115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160
```

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
        180                 185                 190

Tyr Pro Met Val Asp Gly Pro Leu Ser Asn Glu Thr Tyr Ile Gln Ser
            195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Ser Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380

<210> SEQ ID NO 16
<211> LENGTH: 803
<212> TYPE: PRT
<213> ORGANISM: Enterococcus faecalis

<400> SEQUENCE: 16

Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Met Met Tyr Asp
    130                 135                 140

Gly Leu Thr Asp Ala Phe Ser Gly Gln Ala Met Gly Leu Thr Ala Glu
145                 150                 155                 160

```
Asn Val Ala Glu Lys Tyr His Val Thr Arg Glu Gln Asp Gln Phe
            165                 170                 175

Ser Val His Ser Gln Leu Lys Ala Ala Gln Ala Gln Ala Glu Gly Ile
            180                 185                 190

Phe Ala Asp Glu Ile Ala Pro Leu Glu Val Ser Gly Thr Leu Val Glu
            195                 200                 205

Lys Asp Glu Gly Ile Arg Pro Asn Ser Val Glu Lys Leu Gly Thr
210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
            245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
            275                 280                 285

Ala Ile Gln Lys Leu Leu Ala Arg Asn Gln Leu Thr Thr Glu Glu Ile
            290                 295                 300

Asp Leu Tyr Glu Ile Asn Glu Ala Phe Ala Ala Thr Ser Ile Val Val
305                 310                 315                 320

Gln Arg Glu Leu Ala Leu Pro Glu Glu Lys Val Asn Ile Tyr Gly Gly
            325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Lys Tyr Gly Val
            355                 360                 365

Ala Ser Leu Cys Ile Gly Gly Gly Leu Gly Leu Ala Met Leu Leu Glu
            370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
            405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Glu Val Pro Met Gly Val Gly
            435                 440                 445

Leu His Leu Thr Val Asp Glu Thr Asp Tyr Leu Val Pro Met Ala Thr
450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
            485                 490                 495

Val Phe Tyr Asp Val Ala Asp Ala Glu Ser Leu Ile Asp Glu Leu Gln
            500                 505                 510

Val Arg Glu Thr Glu Ile Phe Gln Gln Ala Glu Leu Ser Tyr Pro Ser
            515                 520                 525

Ile Val Lys Arg Gly Gly Gly Leu Arg Asp Leu Gln Tyr Arg Ala Phe
            530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
            565                 570                 575
```

```
Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
        595                 600                 605

Ser Arg Leu Ser Lys Gly Ser Asn Gly Arg Glu Ile Ala Glu Lys Ile
    610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
                660                 665                 670

Lys Glu Gly Arg Tyr Gln Gly Leu Thr Ser Trp Thr Leu Asp Gly Glu
            675                 680                 685

Gln Leu Ile Gly Glu Ile Ser Val Pro Leu Ala Leu Ala Thr Val Gly
        690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
        755                 760                 765

Gly Ala Thr Gly Lys Glu Val Glu Ala Val Ala Gln Gln Leu Lys Arg
770                 775                 780

Gln Lys Thr Met Asn Gln Asp Arg Ala Leu Ala Ile Leu Asn Asp Leu
785                 790                 795                 800

Arg Lys Gln

<210> SEQ ID NO 17
<211> LENGTH: 246
<212> TYPE: PRT
<213> ORGANISM: Saccharomyces cerevisiae

<400> SEQUENCE: 17

Met Ser Leu Pro Phe Leu Thr Ser Ala Pro Gly Lys Val Ile Ile Phe
1               5                   10                  15

Gly Glu His Ser Ala Val Tyr Asn Lys Pro Ala Val Ala Ala Ser Val
                20                  25                  30

Ser Ala Leu Arg Thr Tyr Leu Leu Ile Ser Glu Ser Ser Ala Pro Asp
            35                  40                  45

Thr Ile Glu Leu Asp Phe Pro Asp Ile Ser Phe Asn His Lys Trp Ser
        50                  55                  60

Ile Asn Asp Phe Asn Ala Ile Thr Glu Asp Gln Val Asn Ser Gln Lys
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
        115                 120                 125

Ala Lys Asn Ile Lys Phe Ser Leu Lys Ser Thr Leu Pro Ile Gly Ala
    130                 135                 140
```

```
Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
        195                 200                 205

Gly Asn Ala Leu Leu Phe Glu Lys Asp Ser His Asn Gly Thr Ile Asn
    210                 215                 220

Thr Asn Asn Phe Lys Phe Leu Asp Asp Phe Pro Ala Ile Pro Met Ile
225                 230                 235                 240

Leu Thr Tyr Thr Arg Ile
                245

<210> SEQ ID NO 18
<211> LENGTH: 323
<212> TYPE: PRT
<213> ORGANISM: Sulfolobus solfataricus

<400> SEQUENCE: 18

Met Ile Lys Val Ser Ala Pro Gly Lys Ile Leu Trp Ile Gly Ser Tyr
1               5                   10                  15

Ser Val Val Phe Gly Gly Ile Ser His Val Ile Ala Val Asn Lys Arg
                20                  25                  30

Val Ser Cys Ser Leu Arg Glu Ile Lys Glu Lys Asp Ser Leu Ile Phe
            35                  40                  45

His Thr Ser Tyr Gly His Phe Lys Asn Ser Gly Asn Glu Leu Ile Asn
        50                  55                  60

Ser Val Leu Asp Thr Phe Arg Glu Arg Leu Ser Gln Leu Pro Gln Gly
65                  70                  75                  80

Tyr Glu Ile Asp Leu Tyr Asn Asp Lys Glu Phe Ile Ile Asp Gly Lys
                85                  90                  95

Lys Thr Gly Leu Gly Ser Ser Ala Ala Thr Val Ser Leu Thr Ala
            100                 105                 110

Cys Leu Tyr Tyr Ala Ile His Gly Lys Leu Asp Leu Phe Glu Ile His
        115                 120                 125

Lys Leu Ala Gln Ile Ala Asn Tyr Lys Arg Gln Lys Gly Ile Gly Ser
    130                 135                 140

Gly Phe Asp Ile Ala Ser Ala Val Phe Gly Ser Ile Val Tyr Lys Arg
145                 150                 155                 160

Phe Thr Asp Leu Asp Lys Met Asp Phe Tyr Glu Lys Leu Asn Leu
                165                 170                 175

Gly Asn Tyr Asp Met Met Leu Gly Phe Thr Gly Lys Ser Ser Glu Thr
            180                 185                 190

Val Gly Leu Val Arg Lys Phe Val Glu Lys Ser Asn Leu Asp Asp Phe
        195                 200                 205

Lys Glu Ile Met Arg Leu Ile Asp Glu Glu Asn Tyr Met Ala Ile Lys
    210                 215                 220

Leu Ile Lys Leu Asn Lys Leu Asp Glu Ala Val Glu His Ile Lys Leu
225                 230                 235                 240

Gly Arg Lys Tyr Leu Asn Tyr Ile Ala Glu Arg Ile Val Gly Val Lys
                245                 250                 255

Leu Val Ser Lys Met Glu Glu Glu Leu Ile Lys Ile Ala Glu Glu Glu
            260                 265                 270
```

Gly Ala Leu Val Ala Leu Ser Pro Gly Ala Gly Gly Asp Ser Ile
275                 280                 285

Phe Ala Leu Gly Asn Asp Leu Asn Arg Val Arg Glu Ala Trp Ser Lys
290                 295                 300

Arg Gly Ile Phe Ile Ile Asp Val Lys Glu Asp Glu Gly Leu Arg Leu
305                 310                 315                 320

Glu Ser Asn

<210> SEQ ID NO 19
<211> LENGTH: 396
<212> TYPE: PRT
<213> ORGANISM: Saccharomyces cerevisiae

<400> SEQUENCE: 19

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

```
Ala Phe Ile Tyr Lys Leu Phe Gly Ser Val Pro Gly Trp Asp Lys Lys
            325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
            355                 360                 365

Arg Val Ile Leu Thr Gln Val Gly Ser Gly Pro Gln Glu Thr Asn Glu
            370                 375                 380

Ser Leu Ile Asp Ala Lys Thr Gly Leu Pro Lys Glu
385                 390                 395

<210> SEQ ID NO 20
<211> LENGTH: 182
<212> TYPE: PRT
<213> ORGANISM: Escherichia coli

<400> SEQUENCE: 20

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
            35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
            115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 21
<211> LENGTH: 595
<212> TYPE: PRT
<213> ORGANISM: Populus alba

<400> SEQUENCE: 21

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
            35                  40                  45

Glu Thr Glu Thr Glu Ala Arg Arg Ser Ala Asn Tyr Glu Pro Asn Ser
    50                  55                  60
```

```
Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Leu Glu Leu Ile Asp
                100                 105                 110

Asn Val Gln Arg Leu Gly Leu Gly Tyr Arg Phe Glu Ser Asp Ile Arg
                115                 120                 125

Gly Ala Leu Asp Arg Phe Val Ser Ser Gly Gly Phe Asp Ala Val Thr
130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
                180                 185                 190

Ser Leu Tyr Glu Ala Ser Phe Leu Ala Leu Glu Gly Glu Asn Ile Leu
                195                 200                 205

Asp Glu Ala Lys Val Phe Ala Ile Ser His Leu Lys Glu Leu Ser Glu
210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
                275                 280                 285

Arg Glu Thr Ser Arg Trp Trp Arg Arg Val Gly Leu Ala Thr Lys Leu
                290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
                340                 345                 350

Thr Leu Asp Glu Leu Glu Leu Phe Thr Asp Ala Val Glu Arg Trp Asp
                355                 360                 365

Val Asn Ala Ile Asn Asp Leu Pro Asp Tyr Met Lys Leu Cys Phe Leu
                370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
                435                 440                 445

Pro Leu Gln Leu Val Phe Ala Tyr Phe Ala Val Val Gln Asn Ile Lys
                450                 455                 460

Lys Glu Glu Ile Glu Asn Leu Gln Lys Tyr His Asp Thr Ile Ser Arg
465                 470                 475                 480
```

-continued

```
Pro Ser His Ile Phe Arg Leu Cys Asn Asp Leu Ala Ser Ala Ser Ala
                    485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595
```